United States Patent
De Vlaam et al.

(10) Patent No.: US 10,900,041 B2
(45) Date of Patent: Jan. 26, 2021

(54) ANTISENSE OLIGONUCLEOTIDES FOR USE IN TREATING ALZHEIMER'S DISEASE

(71) Applicant: ProQR Therapeutics II B.V., Leiden (NL)

(72) Inventors: Thomas Petrus Gerardus De Vlaam, Leiden (NL); Tsinatkeab Tadesse Hailu, Leiden (NL); Zhana Karneva, Leiden (NL)

(73) Assignee: PROQR THERAPEUTICS II B.V., Leiden (NL)

( * ) Notice: Subject to any disclaimer, the term of this patent is extended or adjusted under 35 U.S.C. 154(b) by 101 days.

(21) Appl. No.: 15/768,213

(22) PCT Filed: Oct. 14, 2016

(86) PCT No.: PCT/EP2016/074814
§ 371 (c)(1),
(2) Date: Apr. 13, 2018

(87) PCT Pub. No.: WO2017/064308
PCT Pub. Date: Apr. 20, 2017

(65) Prior Publication Data
US 2019/0382772 A1    Dec. 19, 2019

(30) Foreign Application Priority Data

Oct. 16, 2015 (GB) .................................. 1518349.4
Sep. 1, 2016 (GB) .................................. 1614863.7

(51) Int. Cl.
*C12N 15/113* (2010.01)
*C12Q 1/68* (2018.01)

(52) U.S. Cl.
CPC ...... *C12N 15/1138* (2013.01); *C12N 2310/11* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 6,310,048 | B1 | 10/2001 | Kumar |
| 6,531,456 | B1 | 3/2003 | Kurtzman et al. |
| 2014/0039037 | A1 | 2/2014 | Van Roon-Mom et al. |
| 2017/0226521 | A1* | 8/2017 | van Roon-Mom ........... C12N 15/111 |

FOREIGN PATENT DOCUMENTS

| WO | WO-2009/105572 A2 | 8/2009 |
|---|---|---|
| WO | WO-2012/018257 A1 | 2/2012 |
| WO | WO-2015/053624 A2 | 4/2015 |

OTHER PUBLICATIONS

Armbrecht et al. (2015) "Antisense against Amyloid-β Protein Precursor Reverses Memory Deficits and Alters Gene Expression in Neurotropic and Insulin-Signaling Pathways in SAMP8 Mice," J. Alzheimers Dis., 46(2):535-548.
Chakravarthy et al. (2010) "Clinical risk factors for age-related macular degeneration: a systematic review and meta-analysis," BMC Ophthalmology, 10:31.
Chiorini et al. (1999) "Cloning and characterization of adeno-associated virus type 5," J. Virology, 73(2):1309-1319.
Dayton et al. (2012) "The advent of AAV9 expands applications for brain and spinal cord gene delivery," Expert Opinion Biol. Ther., 12(6):757-766.
Ding et al. (2008) "Targeting age-related macular degeneration with Alzheimer's disease based immunotherapies: anti-amyloid-beta antibody attenuates pathologies in an age-related macular degeneration mouse model," Vision Res., 48(3):339-45.
Dorn et al. (2008) "Clinical application of CpG-, non-CpG-, and antisense oligodeoxynucleotides as immunomodulators," Curr. Opin. Mol. Ther., 10(1):10-20.
Egholm et al. (1993) "PNA hybridizes to complementary oligonucleotides obeying the Watson-Crick hydrogen-bonding rules," Nature, 365(6446):566-568.
Fritzsche et al. (2013) "Seven new loci associated with age-related macular degeneration," Nat. Genet., 45(4):433-9, 439e1-2.
Gorman et al. (1998) "Stable alteration of pre-mRNA splicing patterns by modified U7 small nuclear RNAs," Proc. Natl. Acad. Sci. USA, 95(9):4929-34.
Govindaraju et al. (2005) "Backbone-extended pyrrolidine peptide nucleic acids (bepPNA): design, synthesis and DNA/RNA binding studies," Chem. Commun. (Camb.), 28:495-497.
Haass (2004) "Take five—BACE and the gamma-secretase quartet conduct Alzheimer's amyloid beta-peptide generation," EMBO J., 23(3):483-488.
Haass et al. (2012) "Trafficking and proteolytic processing of APP," Cold Spring Harb. Perspect. Med., 2:a006270.
International Search Report for PCT/EP2016/074814, dated Jan. 23, 2017 (5 pages).
Jager et al. (2008) "Age-related macular degeneration," N. Engl. J. Med., 358(24):2606-17.
Konig et al. (1991) "Alternative splicing of the βA4 amyloid gene of Alzheimer's disease in cortex of control and Alzheimer's disease patients," Molecular Brain Research, 9:259-262.
Kumar et al. (2000) "Site-directed antisense oligonucleotide decreases the expression of amyloid precursor protein and reverses deficits in learning and memory in aged SAMP8 mice," Peptides, 21(12):1769-1775.
Love et al. (2015) "Alternative Splicing in Alzheimer's Disease," J. Parkinsons Dis. Alzheimers Dis., 2(2):6.
McCarty et al. (2009) "Mannitol-facilitated CNS entry of rAAV2 vector significantly delayed the neurological disease progression in MPS IIIB mice," Gene Ther., 16(11):1340-52.
Morita et al. (2001) "2'-O,4'-C-ethylene-bridged nucleic acids (ENA) with nuclease-resistance and high affinity for RNA," Nucleic Acid Res. Supplement, 1:241-242.

(Continued)

*Primary Examiner* — Sean McGarry
(74) *Attorney, Agent, or Firm* — Goodwin Procter LLP

(57) ABSTRACT

The invention relates to oligonucleotides suitable for use in treating human disease. More in particular the invention—relates to antisense oligonucleotides suitable for the treatment of Alzheimer's disease.

14 Claims, 13 Drawing Sheets
Specification includes a Sequence Listing.

(56) References Cited

OTHER PUBLICATIONS

Nielsen et al. (1991) "Sequence-selective recognition of DNA by strand displacement with a thymine-substituted polyamide," Science, 254(5037):1497-1500.
Ohno-Matsui (2011) "Parallel findings in age-related macular degeneration and Alzheimer's disease," Prog. Retin. Eye Res., 30(4):217-38.
Panegyres et al. (2011) "The Functions of the Amyloid Precursor Protein Gene and Its Derivative Peptides: I Molecular Biology and Metabolic Processing," Neuroscience & Medicine, 2:120-131.
Puig et al. (2013) "Expression and function of APP and its metabolites outside the central nervous system," Exp. Gerontol., 48(7):608-611.
Ratnapriya et al. (2013) "Age-related macular degeneration—clinical review and genetics update," Clin. Genet., 84(2):160-6.
Sud et al. (2014) "Antisense-mediated Exon Skipping Decreases Tau Protein Expression: A Potential Therapy for Tauopathies," Mol. Ther. Nucleic Acids, 3:e180.
Suter et al. (1999) "Double-target antisense U7 snRNAs promote efficient skipping of an aberrant exon in three human beta-thalassemic mutations," Hum. Mol. Genet., 8(13):2415-23.
Thornton et al. (2005) "Smoking and age-related macular degeneration: a review of association," Eye (Lond), 19(9):935-44.
Van der Kant et al. (2015) "Cellular functions of the amyloid precursor protein from development to dementia," Dev. Cell, 32(4):502-515.
Written Opinion for PCT/EP2016/074814, dated Jan. 23, 2017 (5 pages).
Yoshikai et al. (1991) "Genomic organization of the human-amyloid beta-protein precursor gene," Gene, 102(2):291-292.

\* cited by examiner

FIGURE 2
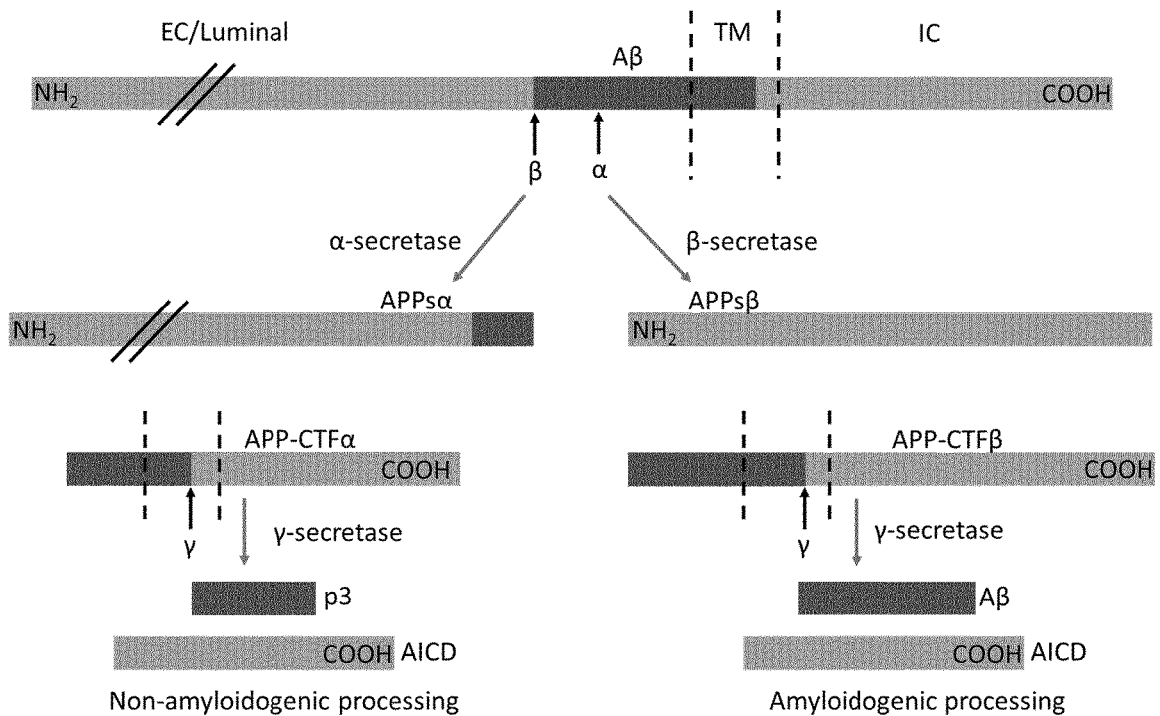
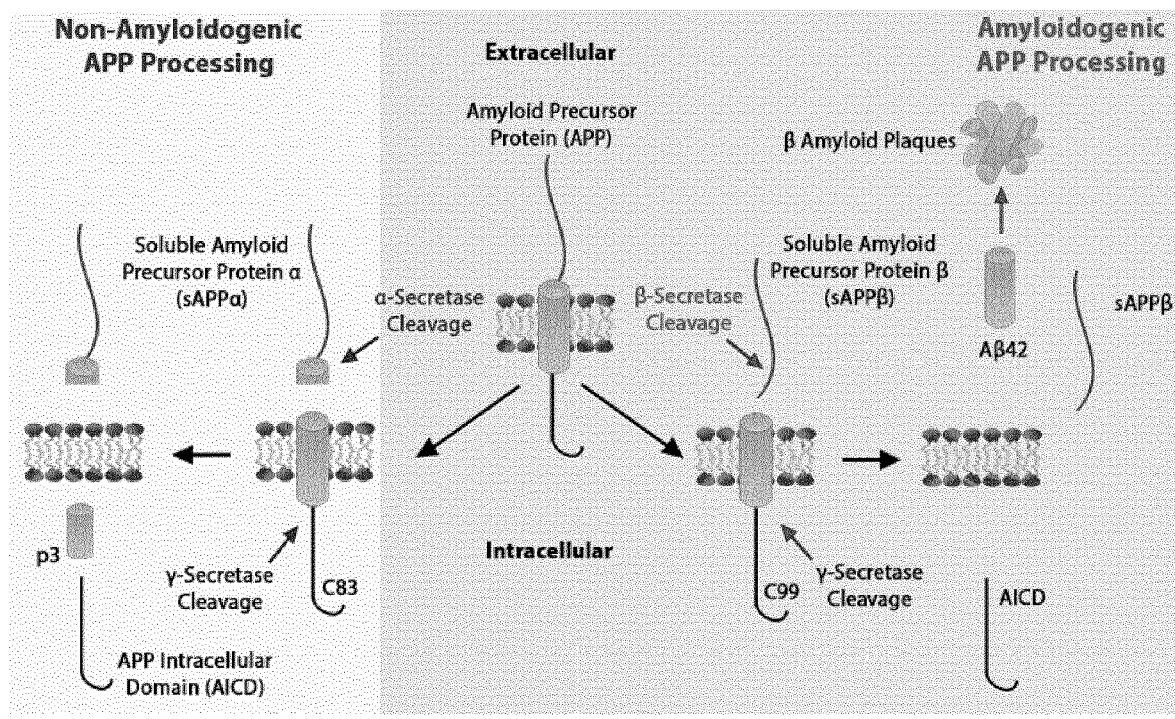

FIGURE 5

```
5' cuuuuucuuaauuuguuuucaagGUGUUCUUUGCAGAAGAUGUGGGUUCAAACAAGGUCAAUCAUUGGACUCAUGGUGGGCGGGUGUGUCAUAAGCGACAGU...
         3' UUCCACAAGAAACGUCUUCUACACCCAAGUUUGUUUCCACGU 5' QRX-203h (42)  (OL1-hRNA/HOL1-RNA)
         3' UUCCACAAGAAACGUCUUCUACACCCAAGUUUGUUUCCA 5' QRX-203h (39)
         3' UUCCACAAGAAACGUCUUCUACACCCAAGUUUGUUU 5' QRX-203h (36)
         3' UUCCACAAGAAACGUCUUCUACACCCAAGUUUG 5' QRX-203h (33)
         3' UUCCACAAGAAACGUCUUCUACACCCAAGU 5' QRX-203h (30)
         3' UUCCACAAGAAACGUCUUCUACACCCA 5' QRX-203h (27)
         3' GACCACAAGAAACGACUUCUACACCCAAGCUUGUUUCCGCGG 5' OL-1
         3' UUCCACAAGAAACGACUUCUACACCCAAGCUUGUUUCCG 5' QRX-203-3m (39)
         3' UUCCACAAGAAACGACUUCUACACCCAAGCUUGUUU 5' QRX-203-3m (36)
         3' UUCCACAAGAAACGACUUCUACACCCAAGCUUG 5' QRX-203-3m (33)
         3' UUCCACAAGAAACGACUUCUACACCCAAGC 5' QRX-203-3m (30)
         3' UUCCACAAGAAACGACUUCUACACCCA 5' QRX-203-3m (27)
                  3' ACUUCUACACCCAA 5' OL-3
                  3' CGUCUUCUACACCCAAGUUUG 5' hAPPEx16_4 (LUMC4)
     3' AAAGUUCCACAAGAAACGUCUU 5' AON1
3' AGAAUUAAACAAAAGUUCCACAAG 5' AON1-1
              3' AGUUCCACAAGAAACGUCUUCUACA 5' AON1-2
         3' ACAAAAGUUCCACAAGAAACGUCUU 5' AON1-3
3' AAACAAAAGUUCCACAAGAAACGACCUCUUCUA 5' AON1-4
                         3' UCUACACCCAAGUUUCUUUCCA 5' AON2
                    3' CCAAGUUUGUUUCCACGUUAGUAA 5' AON3
                              3' AGUAACCUGAGUACCACCCGC 5' AON4
                                      3' CCACAACAGUAUCGCUGUCA 5' AON5
                                3' CGUUAGUAACCUGAGUACCA 5' hAPPEx16_1 (LUMC1)

...GAUCGUCAUCCACCUUGGUGAUGCUGAAGAAGAAACAGUACACACAUCCAUUCAUCAUGGUGGUGGAGguagguaaacuugacugcauguuuccaag 3'
3' CUAGCAGUAGUGGAACCACU 5' hAPPEx16_2 (LUMC2)
       3' CCACUACGACUUCUUCUUGUC 5' hAPPEx16_5 (LUMC5)
                3' CGACUUCUUCUUGUCAUGU 5' AON6
                3' UGUCAUGUGUAGGUAAGUAG 5' AON7
                       3' CAUGUGUAGGUAAGUAGUACCAC 5' hAPPEx16_3 (LUMC3)
                                 3' AGUAGUACCACCACCUCCAUC 5' hAPPEx16_6 (LUMC6)
                                    3' ACCACCUCCAUCCAUUUGAACU 5' AON8
```

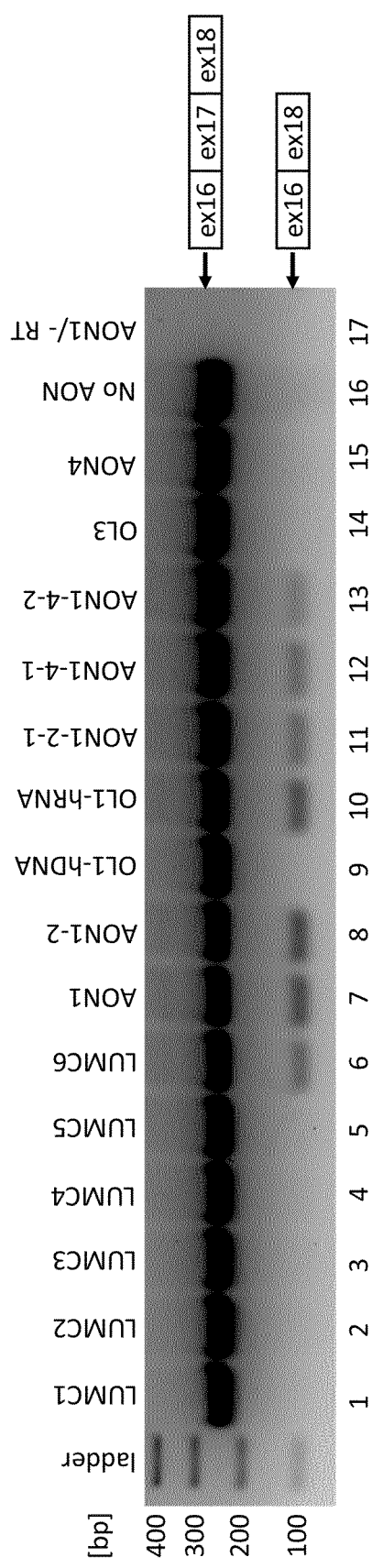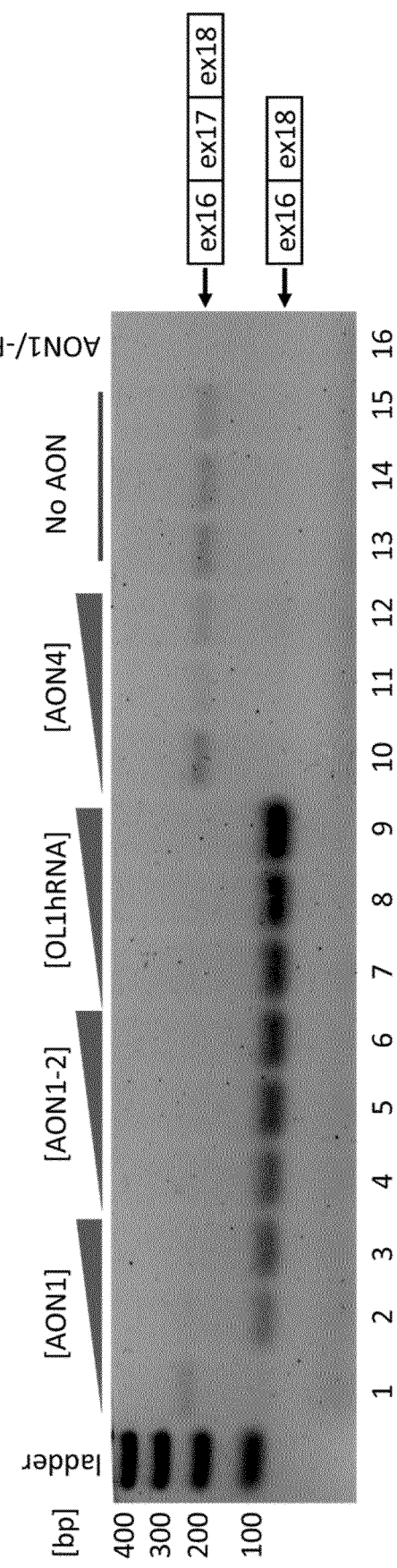

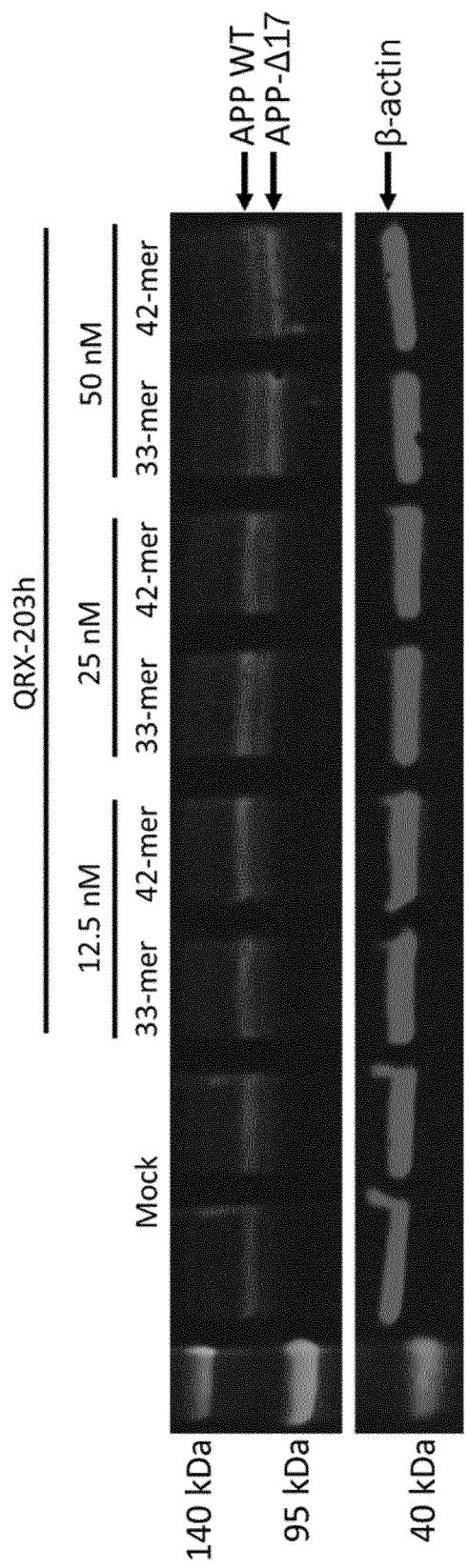
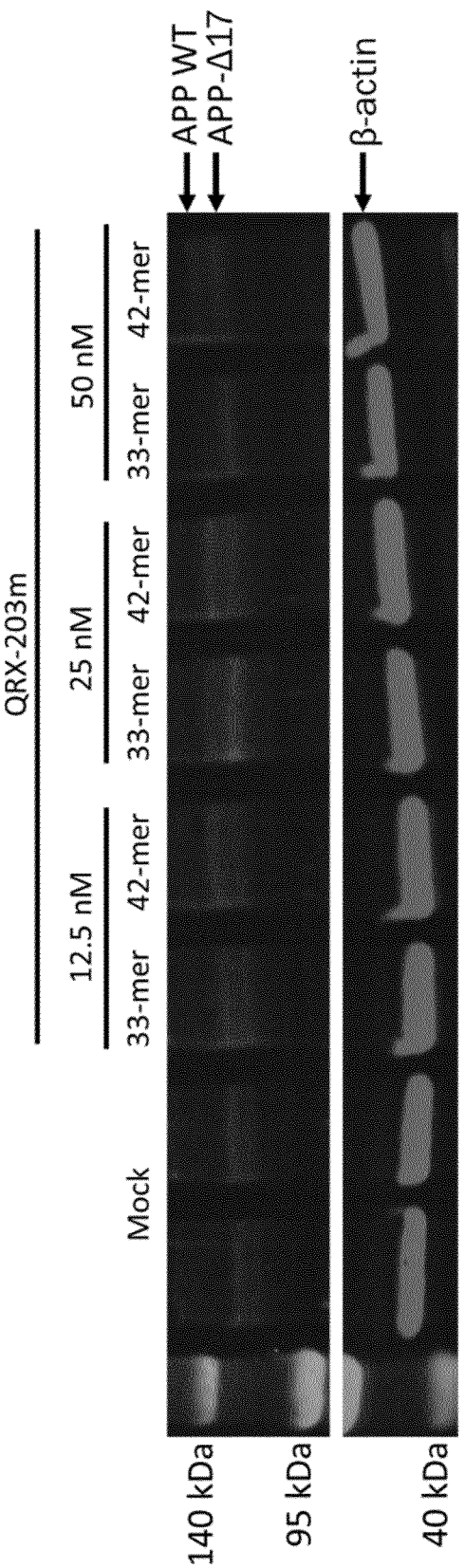

ANTISENSE OLIGONUCLEOTIDES FOR USE IN TREATING ALZHEIMER'S DISEASE

RELATED APPLICATIONS

This application is a § 371 National Stage Application of PCT/EP2016/074814, filed Oct. 14, 2016, which claims priority to and the benefit of United Kingdom patent application No. 1518349.4, filed Oct. 16, 2015, and United Kingdom patent application No. 1614863.7, filed Sep. 1, 2016, the entire disclosures of each of which are incorporated herein by reference for all purposes.

The instant application contains a Sequence Listing which has been filed electronically in ASCII format and is hereby incorporated by reference in its entirety. Said ASCII copy, created on Aug. 9, 2018, is named PQR-010 SL.txt and is 29,105 bytes in size.

FIELD OF THE INVENTION

The present invention is concerned with oligonucleotides suitable for use in treating human disease. More in particular the present invention is concerned with antisense oligonucleotides suitable for the treatment of Alzheimer's disease.

BACKGROUND OF THE INVENTION

Alzheimer's disease (AD) is the most common form of dementia and responsible for 60-70% of all dementia cases (WHO Dementia Factsheet; who.int/mediacentre/factsheets/fs362/en/). Extracellular amyloid plaques and intracellular neurofibrillar tangles are the classic neuropathological hallmarks of AD. The extracellular plaques are mainly composed of insoluble aggregates of secreted amyloid β (Aβ) peptides that are a result of sequential cleavage with proteases known as secretases on the amyloid precursor protein (APP). APP is a type-I integral membrane protein with a large N-terminal extracellular or luminar domain and a short C-terminal domain in the cytosol. The human APP gene contains 18 exons. Alternative splicing of APP pre-mRNA generates several different isoforms that are differentially expressed (Yoshikai et al. 1991. Gene 102(2): 291-292). The three major isoforms are APP770, APP751 and APP695 (FIG. 1). APP695 is the main isoform expressed in neuronal cells while APP770 and APP751 are widely expressed in non-neuronal cells. A distinct feature of APP isoforms expressed in the central nervous system is the absence of a KPI domain, which is encoded by exon 7 (APP714).

While the function of APP has been intensely investigated in the context of the brain-specific isoform APP695, other APP isoforms are widely expressed throughout the body (Puig and Combs 2013. Exp Gerontol 48(7):608-611). These include APP770, APP751 which lack exon 8, APP714 and APP639 which are expressed in fetal tissues and adult liver. In addition, the Leokocyte-derived L-APP variants which lack exon 15 are highly expressed in leukocytes and are upregulated in activated astrocytes and microglial cells.

While both the C- and N-terminal domains of APP are proposed to be involved in numerous cellular functions, it is still a matter of debate if they function in the context of holo-APP, after specific cleavage events or in both (Van der Kant and Goldstein 2015. Dev Cell 32(4):502-515). The N-terminus is structured and more divergent between APP family members and within different isoforms, possibly pointing to divergent and localization-specific roles. On the other hand, the C-terminus shows a high degree of conservation, indicative of an evolutionarily conserved and critical function. The N-terminus of APP770, which is expressed in different tissues contains two dimerization domains, an acidic domain, a Kunitz protease inhibitor (KPI) region and an OX-2 domain for glycan attachment. In contrast, the brain-specific APP695 lacks both the KPI and OX-2 domains. The dimerization domains, in addition to allowing homo- and heterodimerization with different family members can bind heparin, copper and zinc.

Several functions have been proposed for APP based on indirect and direct observations. One of the first proposed functions is as a cell surface receptor because it has similar secondary structures and proteolytic processing profile as the Notch receptor. Another function ascribed to APP is in cell and synaptic adhesion. This is suggested by data that show that APP extracellular domains, particularly the dimerization domains, interact with extracellular matrix proteins and heparin sulphate proteoglycans. In addition, the dimerization domains found on the extracellular domains of APP may mediate cell-cell interaction via a homo or heterophillic interaction. Mutagenesis studies in cell cultures have shown that conserved sequence motifs on the luminal (or extracellular) side of APP are important for dimerization. Mutagenic alteration of these motifs leads to loss of dimerization, disruption of cell-cell and cell-matrix adhesion, and production of shorter forms of AP peptide. Additionally, a tetra-peptide "RHDS" motif (SEQ ID NO: 61) near the N-terminus of the AP sequence appears to promote cell-cell adhesion in an integrin-homologous (RGD) manner. This is further supported by co-localization observations of APP with integrins on the cell surface of axons at sites of adhesion and siRNA silencing of APP during development which leads to defects in neuronal migration. Finally, heterologous expression of affinity-tagged APP in mice, followed by interactome analysis has identified several interacting partners, with several of them potentially being functionally relevant interactions.

APP undergoes proteolytic processing through two major pathways (Haass 2004. EMBO J 23(3):483-488; Haass 2012. Cold Spring Harb Perspect Med 2: a006270). The production of Aβ in the amyloidogenic pathway results from the sequential cleavage of APP by β-secretase and γ-secretase. Initial cleavage by β-secretase at the beginning of the Aβ fragment generates a large soluble amino terminal fragment (APPsβ) and a membrane tethered C-terminal fragment (APP-CTFβ/C99). C99 is further processed by a membrane-associated multi-subunit enzyme complex (γ-secretase) generating an amyloid intracellular domain (AICD) and a secreted Aβ peptide of varying lengths depending on the exact position of γ-cleavage (FIG. 3). In comparison, the non-amyloidogenic cleavage of APP is first mediated by α-secretase which cleaves APP in the middle of the Aβ region releasing a large N-terminal fragment and a membrane bound fragment (APP-CTFα/C83) lacking the amino terminus of the Aβ peptide. Subsequent processing by γ-secretase results in the liberation of a p3 peptide which is made up of the C-terminus of the Aβ fragment and AICD. Such regulated intramembrane proteolysis and sequential release of fragments of APP has been implicated in various signalling pathways.

Kumar and colleagues (Kumar et al. 2000. Peptides 21(12):1769-1775) and U.S. Pat. No. 6,310,048 describe an antisense oligodeoxynucleotide sequence referred to as OL-1, that targets the Aβ peptide from the α-secretase site downstream to roughly half-way the Aβ peptide. It is suggested that this DNA oligonucleotide reduces production of the Aβ peptide, while leaving part or all of the upstream portions of the APP intact. This result is reportedly seen both in APP-cDNA transfected HeLa cells, as well as in a SAMP8 mouse that spontaneously overexpresses APP. This patent disclosure is silent on the mechanism by which this truncated protein is produced, nor does it disclose the exact boundaries of the protein. Whatever the mechanism, in a follow-on study, the authors report that the same antisense oligodesoxynucleotide sequence OL-1 causes reduction of APP expression but no reduction of Aβ in the brain of SAMP8 mice (Armbrecht et al. 2015. J Alzheimers Dis 46(2):535-548).

While references mentioned herein provide interesting insights into the possibilities of an oligonucleotide-based approach to treat Alzheimer's disease, no clear mechanism is postulated, so it remains unclear what proteins actually result from this intervention. The effect in cDNA transfected HeLa cells cannot be based on an exon skipping mechanism, as the cDNA does not contain introns. In contrast, the group of Schellen berg (Sud et al. 2014. Mol Ther Nucleic Acids 3:e180) has recently shown that antisense oligonucleotides (AONs) can be used to facilitate exon skipping to omitting exons that harbor pathologic mutation in the microtubule associated protein tau (MAPT) and suggested that such a strategy could be used to treat Alzheimer's disease. Despite good progress in the art, there remains a need for new approaches to prevent and/or treat Alzheimer's disease, which circumvents some of the concerns associated with the approaches described in the prior art.

SUMMARY OF THE INVENTION

The invention provides an antisense oligonucleotide (AON) capable of preventing or reducing exon 17 inclusion into a human APP mRNA, when said mRNA is produced by splicing from an APP transcript in a human cell; characterized in that said AON is capable of binding to and/or is complementary to a region within the 5' part of exon 17 and/or the 3' region of intron 16 of the human APP gene.

Useful oligonucleotides are AONs that bind to a region starting 18 nucleotides upstream of the intron16/exon17 junction and terminating 40 nucleotides downstream of the intron16/exon17 junction. Such AONs include those having a sequence selected from SEQ ID NOs: 9, 17, 18, 19, 20, 28, and 29.

Preferred AONs are oligoribonucleotides, and ideally these have internucleosidic linkages which are chemically modified (preferably with phosphorothioate-linkages). Modification of the ribose sugar is also useful e.g. with a 2'-O-alkyl modification (ideally 2'-O-methyl).

A particularly useful AON is an oligoribonucleotide having nucleotide sequence SEQ ID NO: 29 with phosphorothioate inter-nucleotide linkages and 2'-OMe sugars. This 42-mer oligonucleotide is herein referred to as 'HOL1-RNA', 'OL1 hRNA' or 'QRX-203h (42)', wherein the number between parentheses indicates the number of nucleosides. Other preferred AONs as disclosed herein are AONs that are shorter versions of QRX-203h (42) wherein the AON is shortened at the 5' end; preferred examples are QRX-203h (39) (SEQ ID NO; 37), QRX-203h (36) (SEQ ID NO: 38), QRX-203h (33) (SEQ ID NO: 39), QRX-203h (30) (SEQ ID NO: 40) and QRX-203h (27) (SEQ ID NO: 41).

These AONs can be formulated in pharmaceutical compositions for preventing or reducing exon 17 inclusion into a mammalian, preferably human APP mRNA. Thus they can be used for treating or preventing Amyloid beta (Aβ) associated diseases such as CAA (Cerebral Amyloid Angiopathy) and Alzheimer's disease. The invention also provides an internally truncated and isolated APP protein known as APP646.

DESCRIPTION OF THE FIGURES

FIG. 2: Amyloid precursor protein (APP) processing pathways. Two principal pathways—the nonamyloidogenic (α-secretase) pathway and the amyloidogenic β-secretase pathway, can process the single-pass transmembrane protein APP. In the non-amyloidogenic pathway, α-secretase cleaves in the middle of the β-amyloid (Aβ) region to release the soluble APP-fragment sAPP-α. The APP C-terminal fragment 83 (APP-CTF83) is then cleaved by γ-secretase to release the APP intracellular domain (AICD) and P3 fragment. In the amyloidogenic pathway, β-secretase cleaves APP to produce the soluble fragment sAPP-β. APP-CTF99 is subsequently cleaved by γ-secretase to produce Aβ and AICD (from Haass 2004).

FIG. 3 discloses "TEEISEVKMDAEFR", "HQKLV", "VGSNK", "TVIVITLVMLKKKQY", "EQMQN", and "VGSNKGAIIGLMVGGVVIATVIV-ITLVMLKKKQY" as SEQ ID NOS 54-59, respectively.

FIG. 4 discloses the first sequence as SEQ ID NO: 52, and the second sequence (without exon 17) as SEQ ID NO: 53.

FIG. 5: Localization of the various AONs tested herein in relation to exon 17 of human APP and the regions flanking it (intron 16 (lower case) -exon 17 (upper case) -intron 17 (lower case)) (SEQ ID NO: 60). AONs spanning APP exon 17 and flanking intron-exon junctions were designed and screened for exon 17 skip potential. Shown are the sequence details and names of the AONs screened, aligned with the target. AONs are given from 3' (left) to 5' (right), whereas the intron16-exon17-intron17 sequence is provided from 5' (left) to 3' (right). FIG. 5 also discloses SEQ ID NOS 29, 37-41, 28, 42-46, 30, 24, 9, 17-20, 10-13, 21-22, 25, 14-15, 23, 26, and 16, respectively, in order of appearance.

FIG. 7: AON mediated skipping by AONs of the present invention. SK-N-SH cells were reverse transfected with various concentrations of AONs and incubated for 6 hours. After 6 hours, old media was removed and replaced with fresh media and incubation continued for a further 42 hours. RNA isolation, cDNA synthesis and PCR was performed as described in the examples. Under this optimized conditions, AONs AON1, AON1-2 and OL1-hRNA (lanes 1-9) result in a near complete skipping of APP exon 17 under all concentrations tested (25, 50 and 100 nM) while the controls AON4 and No AON (lanes 10-12) did not. This shows that the AONs of the present invention, in SK-N-SH cells, are extremely effective in achieving the desired outcome and may even be potent at much lower concentrations under prolonged treatment.

DETAILED DESCRIPTION OF THE INVENTION

The inventors of the present invention sought to develop a strategy that will maintain the physiological roles of APP as a holo-protein or its secreted soluble cleavage products while reducing or eliminating the inclusion/production of the Aβ peptide fragment. As such, the basis of the strategy is based on allowing the expression of APP without part of the Aβ segment, by skipping exon 17 in any APP pre-mRNA isoform known to exist.

A strategy that is used to alter gene expression and the production of a specific protein is the use of modified antisense oligonucleotides (AONs) that bind the target sequence, preferably in standard Watson-Crick fashion, to interfere with RNA transcription, pre-mRNA splicing or mRNA translation. AONs that cause the skip of exons that harbor pathologic mutations are currently being trialed to treat Duchenne Muscular Dystrophy (DMD). A prerequisite for this approach is that the exons flanking the exon to be skipped are in frame. In other words, joining of flanking exons should not interrupt the reading frame of the full length protein, to avoid incorporation of downstream codons coding for different amino acids than the wild-type protein, or even stop codons. Recently, Sud et al. (2014) demonstrated that AON-mediated exon skipping leads to mRNA reduction of the microtubule associated protein tau (MAPT) by up to 50% with a corresponding downregulation of tau protein levels of up to 80%. In this study, AON-mediated exon skipping of exons 1, 5, or 7 of MAPT results in a frameshift that leads to a downstream premature stop codon initiating nonsense-mediated decay.

Figure 1:
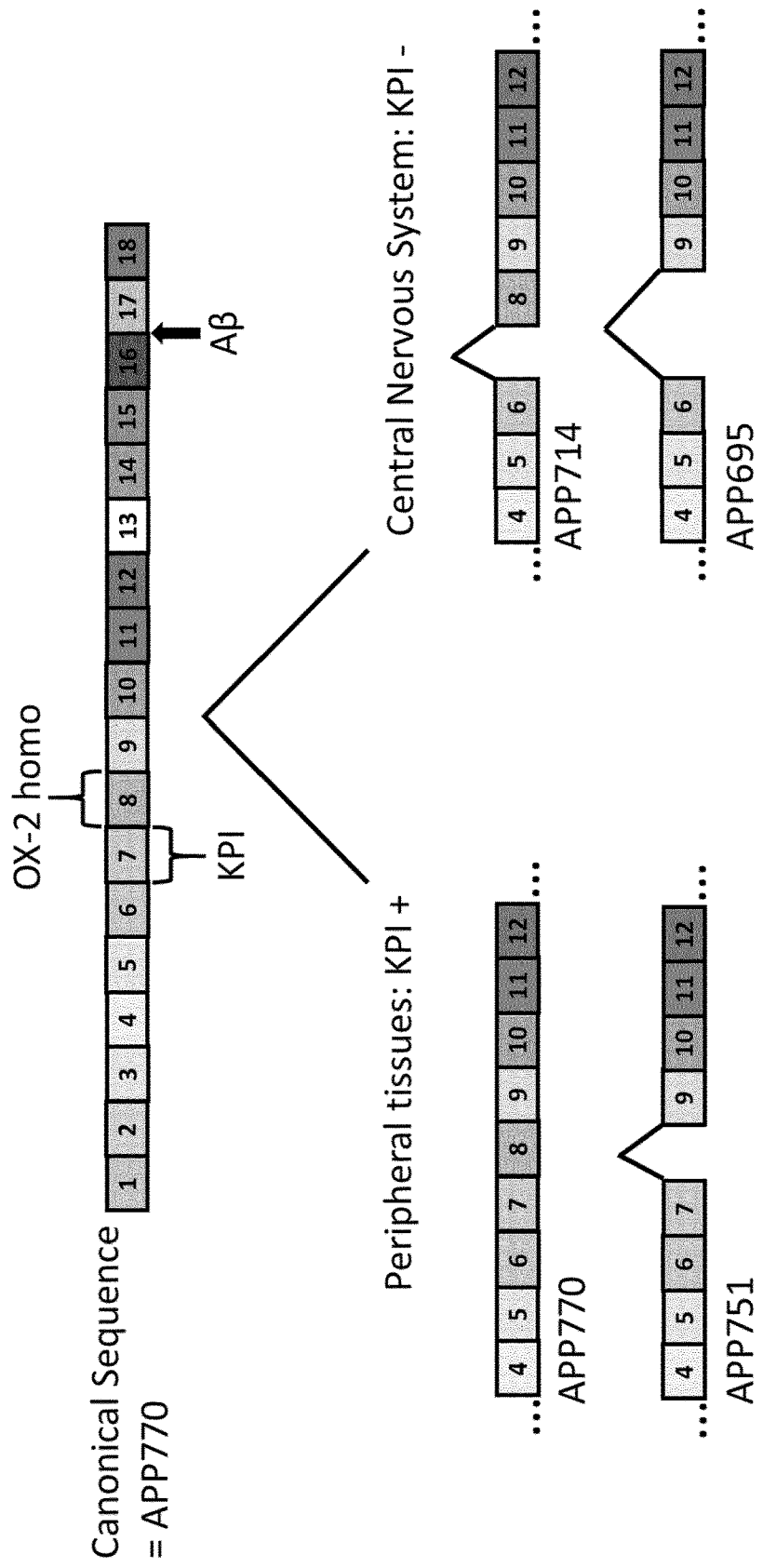
FIG. 1: Exon structure of APP transcripts generated by alternative splicing of exons 7 and 8. The KPI segment is coded by exon 7. Transcripts with exon 7 are found in peripheral organs while those lacking exon 7 are expressed in the central nervous system (CNS). APP714 is highly expressed in fetal CNS while APP695, which also lacks exon 8, is expressed in adult CNS. The Aβ encoding sequence is found between exon 16 and 17. Adapted from http://file.scirp.org/Html/10-2400027_5533.htm.
Figure 3:
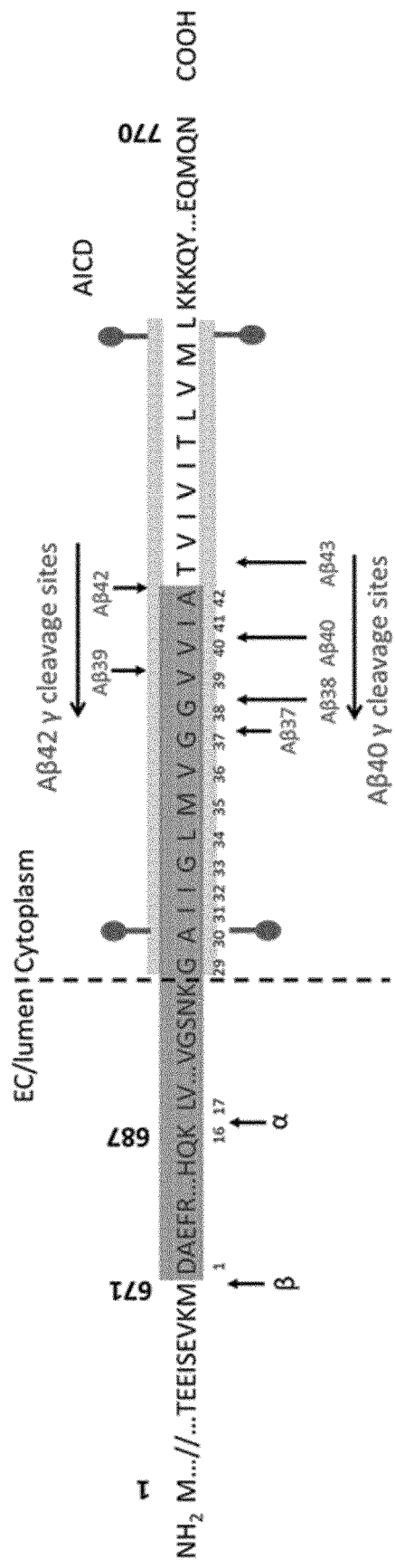
FIG. 3: Organization of the various secretase cleavage sites in relation to the Aβ fragment and the transmembrane domain of APP. The variable γ-cleavage sites lead to the production of different Aβ fragment lengths with different biophysical properties. The Aβ42 process sing events are more amyloidogenic compared to the Aβ40 cleavage events. Mutations on APP close to the amino-terminus of the Aβ fragment have been shown to alter γ-secretase cleavage events either leading to increased or decreased production of Aβ42.
Figure 4:
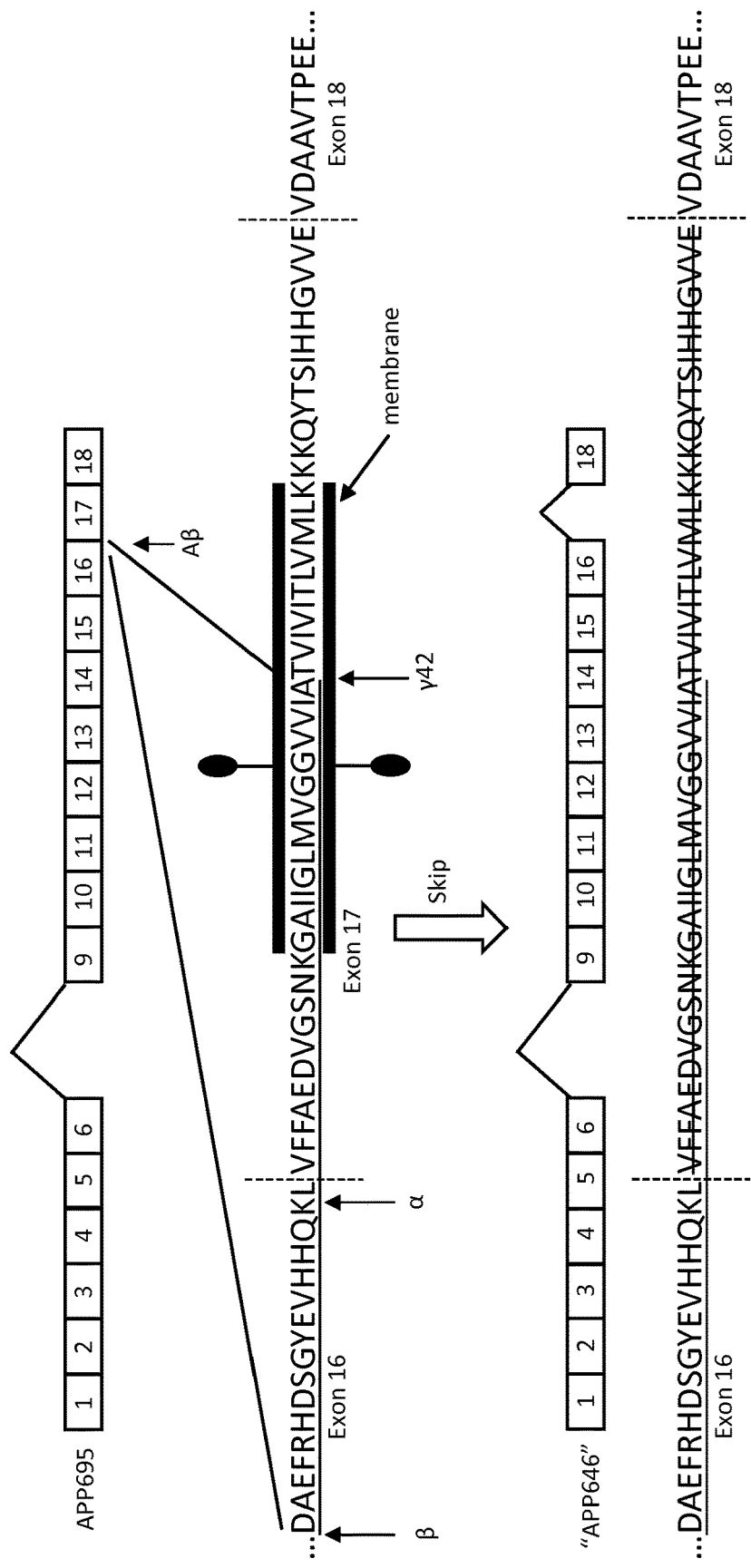
FIG. 4: Exon skipping strategy to prevent the formation of aggregation prone full-length Aβ peptides in the CNS. Upward arrows indicate the most common α-, β- and γ-secretase cleavage sites. Cleavage by β-secretase followed by γ-secretase activity leads to the generation of an Aβ42 fragment (underlined sequence). The skipped exon (exon 17) is amino acids 608-656 of SEQ ID NO: 5 and shown in strikethrough (SEQ ID NO: 6). Skipping exon 17 will result in the removal of the amyloidogenic γ-cleavage site while leaving the α-cleavage site responsible for the generation of soluble APPα intact. The amino acid sequence of this internally truncated "APP646" protein is SEQ ID NO: 4.

The inventors of the present invention sought to exploit the potential of exon skipping AONs as a more subtle strategy to address Alzheimer's disease than translation stop or, RNase H mediated knock down, or non-sense mediated decay. The approach exploits skipping exon 17 of APP (numbered according to the canonical nomenclature of APP: FIG. 1). In this scenario, a protein made by skipping exon 17 will have the following features:

1. Exon 16 is joined with exon 18, maintaining the reading frame and resulting in a protein with 646 amino acids which was named "APP646" herein.
2. Considering the linear sequence of the amino acids, the positions of β and α secretase cleavage sites remain intact while the γ cleavage site is removed.
3. The transmembrane domain, which is all within exon 17, is removed.
4. The C-terminal portion of the Aβ peptide (GAIIGLMVGGVVIA; SEQ ID NO: 2), which is embedded within the membrane, is removed.

Figure 6A:
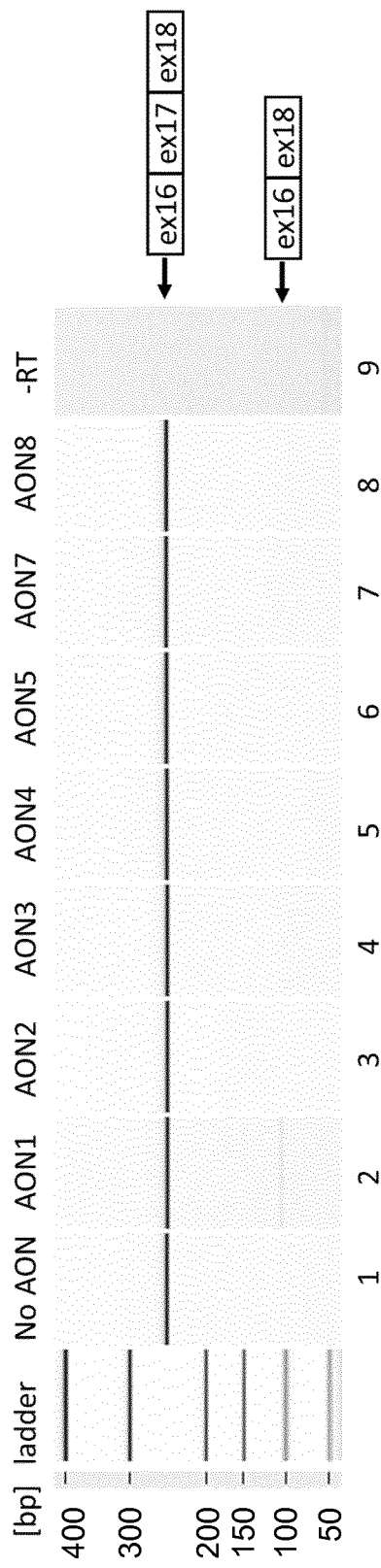
FIG. 6: AON mediated skipping of exon 17 of APP. Total RNA was isolated from cells 24 hours post transfection and PCR performed in a two step RT-PCR reaction. Products were amplified using primers binding on exon 16 (forward) and exon 18 (reverse). The band near the 100 bp marker shows exon 17 skipping while the band between the 200 and 300 bp markers is amplification of unskipped products. Lanes 1 to 8 in (A) and lanes 1 to 5 in (B) are AONs according to the invention (see also Table 1). The other lanes are controls without AON treatment or reverse transcriptase for cDNA synthesis (−RT), respectively. Each of the AONs of the present invention exhibit a modest percentage of skipping, despite the fact that conditions were not optimized. (C): In a repeat experiment the best performing AONs (AON1, AON1-2,) as well as two new AONs (AON1-2-1, and AON1-4-2) and a mismatch corrected AON1-4 (AON1-4-1) were tested side-by-side with a humanized version of the OL-1 DNA AON (referred to in the figure as OL1-hDNA), the OL3 RNA AON (referred to as OL3), the humanized RNA PS, 2'-OMe AON based on OL1-hDNA AON (in this figure referred to as OL1-hRNA), and the PS, 2'-OMe RNA versions of the six AONs disclosed in WO 2012/018257 (see also Table 3; herein referred to as hAPPEx16_1 to 6, but renamed LUMC1 to 6 in this figure), and AON4 or no AON as negative controls. As can be seen, none of the AONs disclosed in the prior art performed (as good) as the AONs according to this invention. LUMC1-5 (corresponding to hAPPEx16_1 to 5, respectively) did not give any skipping of exon 17; LUMC6 exhibited modest skipping of exon 17. The DNA oligos OL1-hDNA (the humanized version of OL1 disclosed in the prior art) and OL3 did not show any exon 17 skipping. For sake of completeness, the mouse version OL1 DNA AON, having 4 mismatches to the human APP target sequence, was tested and it was found that this AON did not give exon 17 skip (data not shown). In this particular experiment, the RNA PS 2'-OMe AON OL1-hRNA provided the best exon 17 skip efficiency.

WO 2012/018257 proposes skipping exons harboring proteolytic cleavage sites, trinucleotide repeat expansions or mutations in the context of neurodegenerative disease. In table 3 herein, six PS 2'-OMe AONs directed at exon 16 (which is believed to be exon 17 according to the canonical numbering used herein) of the human APP sequence. No data are presented in WO 2012/018257 whether these AONs produce the desired result. The present inventors have tested these AONs side-by-side with the AONs according to the present invention and identified one AON (hAPPEx16_6 or LUMC6) that produces a skip of exon 17 (FIG. 6C), albeit with a lower efficiency than the AONs designed for the first time by the present inventors; the other five AONs disclosed in WO 2012/018257 did not produce the expected skip, or any skip at all.

fused in the correct reading frame to exon 18. As a consequence, a truncated protein is produced harbouring the α-secretase cleavage site, known to be used in neuronal cells in the adult human brain, to cleave amyloid α protein from holo-APP. The inventors of the present invention postulate a normal function of this artificially created APP646 protein. However, the Aβ peptide, associated with the development of Alzheimer's disease, will no longer be produced from the APP646 protein, since the γ-secretase site is lost in APP646.

Proteolytic processing by β- and α-secretase of APP646 will result in the production of the amino-terminal sAPPβ and sAPPα segments, respectively, as well as the corresponding carboxyl-terminal APP-CTFβ and APP-CTFα. At the same time, because of the removal of the natural amyloidogenic γ-secretase sites, the production of Aβ peptides following β-processing is avoided.

This process is known to occur in nature in an overwhelming number of genes, under the influence of factors associated with the differentiation state of a cell, age, nutritional state and other chemical or biological factors. Pre-mRNA splicing can also be manipulated at will, for example by modulating splice site selection by the endogenous splicing machinery. Splice site selection can, for example, be modulated using AONs that interfere with binding of components of the splicing machinery to a splice site, a so-called branch point, a polypyrimidine tract, and/or regions affecting splice site selection. Such regions are known as splicing enhancers and splicing silencers, which may be located either in exons or introns. Hence, there are intronic and exonic splice site enhancers (ISEs and ESEs) and intronic or exonic splice site silencers (ISSs and ESSs). It is possible to modulate splicing also in a (semi)-quantitative fashion.

The inventors of the present invention have tested a number of AONs binding to sequences located inside exon 17, as well as to sequences bridging intron 16 and exon 17 (see Table 1).

TABLE 1

First batch of AONs designed and tested for exon skipping efficiency (SEQ ID NOS 62-69, left column; SEQ ID NOs: 9-16, right column); see FIG. 6A for results. The lower case sequence in AON1 represents the intron 16 sequence; the lower case sequence in AON8 represents the intron 17 sequence; the upper case in all sequences represent exon 17 sequences (see FIG. 5). The underlined C in AON2 was introduced erroneously.

| Identifier | target sequence (5' to 3') | antisense sequence (5' to 3') |
| --- | --- | --- |
| AON1 | uuucaagGUGUUCUUUGCAGAA | UUCUGCAAAGAACACcuugaaa |
| AON2 | AGAUGUGGGUUCAAACAAAGGU | ACCUUUCUUUGAACCCACAUCU |
| AON3 | GGUUCAAACAAAGGUGCAAUCAUU | AAUGAUUGCACCUUUGUUUGAACC |
| AON4 | UCAUUGGACUCAUGGUGGGCG | CGCCCACCAUGAGUCCAAUGA |
| AON5 | GGUGUUGUCAUAGCGACAGU | ACUGUCGCUAUGACAACACC |
| AON6 | GCUGAAGAAGAAACAGUACA | UGUACUGUUUCUUCUUCAGC |
| AON7 | ACAGUACACAUCCAUUCAUC | GAUGAAUGGAUGUGUACUGU |
| AON8 | UGGUGGAGguagguaaacuuga | ucaaguuuaccuacCUCCACCA |

Surprisingly, it was found that by targeting sequences in the region spanning the transition intron 16/exon 17, using AONs capable of binding to these sequences, exon 17 can be prevented from being included in the mature mRNA. This process (exon skipping) yields a mRNA wherein exon 16 is On the basis of the results of the first experiment, further AONs were designed leaving part of the sequence of AON1 intact, adding sequences upstream or downstream thereof, thereby shifting the binding position to the left (upstream) or the right (downstream) in the target sequence. See Table 2.

TABLE 2

Figure 6B:
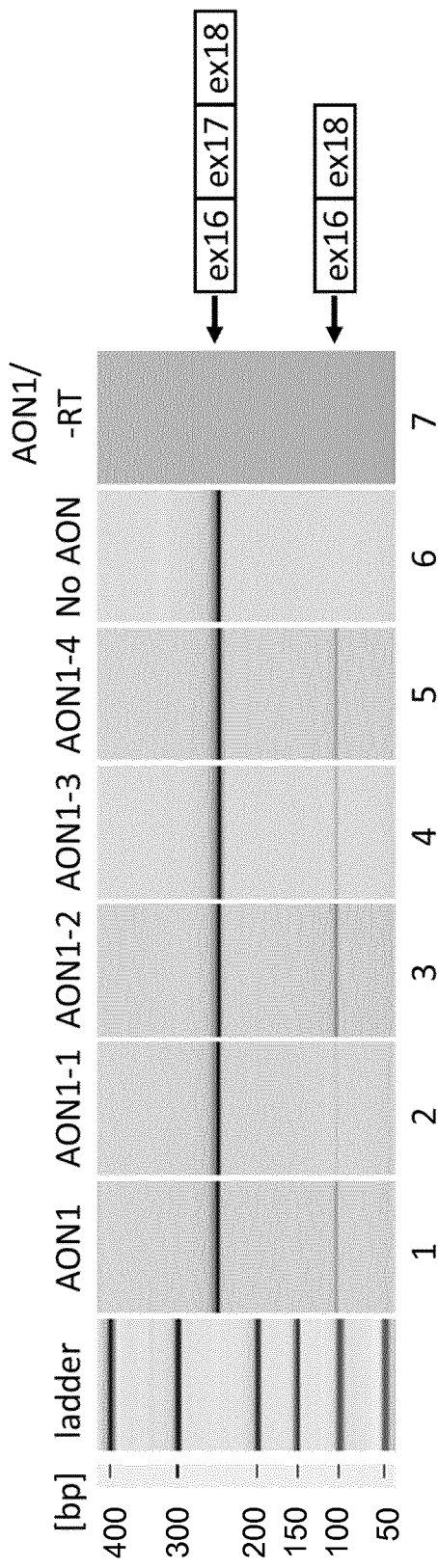

AON1 and sequence modifications thereof (SEQ ID NOS 62 and 70-73, left column; SEQ ID NOs: 9 and 17-20, right column); see FIG. 6B for results. The lower case sequences represent the intron 16 sequences (see FIG. 5). The underlined C in AON1-4 was introduced erroneously.

| Identifier | target sequence (5' to 3') | antisense sequence (5' to 3') |
|---|---|---|
| AON1 | uuucaagGUGUUCUUUGCAGAA | UUCUGCAAAGAACACcuugaaa |
| AON1-1 | ucuuaauuuguuuucaagGUGUUC | GAACACcuugaaaacaaauuaaga |
| AON1-2 | ucaagGUGUUCUUUGCAGAAGAUGU | ACAUCUUCUGCAAAGAACACcuuga |
| AON1-3 | uguuuucaagGUGUUCUUUGCAGAA | UUCUGCAAAGAACACcuugaaaaca |
| AON1-4 | uuuguuuucaagGUGUUCUUUGCAGAAGAU | AUCUUCUGCAAAG<u>C</u>AACACcuugaaaacaaa |

In addition, the inventors of the present invention tested AONs disclosed in the prior art (WO 2012/018257): hAPPEx16_1-hAPP Ex16_6, SEQ ID NOS: 21-26, which are PS 2'-OMe oligoribonucleotides) and in U.S. Pat. No. 6,310,048 (OL-1 and OL-3, SEQ ID NOS: 27 & 30, which are both 'mouse' antisense oligodeoxyribonucleotides, binding to exonic sequences of exon 17 of human APP, with 4 mismatches due to sequence divergence between mouse and humans). In addition, the inventors of the present invention generated a 'humanized' oligoribonucleotide version of OL-1, coined OL1-hRNA (or HOL1-RNA or QRX-203h (42)), with a perfect match to the human APP sequence and, in addition, PS 2'-OMe chemistry. The results of the comparative skipping test are depicted in FIG. 6C. The (mouse) OL1-RNA AON was tested and shows a reasonable level of exon 17 skipping, yet the human OL1-RNA version shows superior skipping efficiency. Then, a panel of AONs with an incubation time of 48 h was tested. OL1-hRNA showed complete exon 17 skipping, with no trace of the non-skipped amplification product visible in a agarose gel (FIG. 7).

In therapeutic settings it is preferred to use AONs that are as short as possible, while maintaining a specific effect. Also, shorter AONs have the benefit of being cheaper in production and have a lower amount of erroneously produced by-products. For this, the inventors reasoned that the QRX-203h (42) AON may be shortened while maintaining a strong effect on APP exon 17 skipping. Hence, further AONs were generated that were shortened at the 3' terminus, based on QRX-203h (42). Shortening was done by 3 nucleotides with each AON, resulting in QRX-203h (39), QRX-203h (36), QRX-203h (33), QRX-203h (30) and QRX-203h (27). The sequences and the positions on the APP pre-mRNA where these additional are targeted is shown in FIG. 5.

Table 3 provides the sequences of the various AONs that were tested herein, with their respective SEQ ID NO. These are aligned with the target sequence in FIG. 5. Please note, that the canonical sequence numbering is maintained, i.e. numbering the exons in the human APP from 1 to 18, as they occur in the gene. Hence, exon 17 remains exon 17 in the neuronal RNA transcript, despite the fact that the neuronal APP transcript is lacking exon 7 and 8 due to (natural) alternative splicing.

TABLE 3

AONs that were tested for exon 17 skipping. The lower case sequence in AON1, AON1-1, AON1-2, AON1-3 and AON1-4 represent the corresponding intron 16 sequences; the lower case sequences in hAPPEx16_6 (LUMC6) and AON8 represent the corresponding intron 17 sequence; the upper case in all sequences represent corresponding exon 17 sequences, except for the underlined C in AON1-4 that was introduced erroneously. OL-1 hRNA/HOL1-RNA is also referred to herein as QRX-203h (42).

| Name | Sequence | SEQ ID NO: |
|---|---|---|
| OL-1 DNA mouse | 5' GGCGCCTTTGTTCGAACCCACAUCTTCAGCAAAGAACACCAG 3' | 27 |
| OL-1 RNA mouse | 5' GGCGCCUUUGUUCGAACCCACAUCUUCAGCAAAGAACACCAG 3' | 28 |
| OL-1 hRNA/HOL1-RNA | 5' UGCACCUUUGUUUGAACCCACAUCUUCUGCAAAGAACACCUU 3' | 29 |
| OL-3 | 5' AACCCACAUCUUCA 3' | 30 |
| hAPPEx16_1 (LUMC1) | 5' ACCAUGAGUCCAAUGAUUGC 3' | 21 |
| hAPPEx16_2 (LUMC2) | 5' UCACCAAGGUGAUGACGAUC 3' | 22 |
| hAPPEx16_3 (LUMC3) | 5' CACCAUGAUGAAUGGAUGUGUAC 3' | 23 |
| hAPPEx16_4 (LUMC4) | 5' GUUUGAACCCACAUCUUCUGC 3' | 24 |
| hAPPEx16_5 (LUMC5) | 5' CUGUUUCUUCUUCAGCAUCACC 3' | 25 |
| hAPPEx16_6 (LUMC6) | 5' cuacCUCCACCACACCAUGAUGA 3' | 26 |
| AON1 | 5' UUCUGCAAAGAACACcuugaaa 3' | 9 |

TABLE 3-continued

AONs that were tested for exon 17 skipping. The lower case sequence in AON1, AON1-1, AON1-2, AON1-3 and AON1-4 represent the corresponding intron 16 sequences; the lower case sequences in hAPPEx16_6 (LUMC6) and AON8 represent the corresponding intron 17 sequence; the upper case in all sequences represent corresponding exon 17 sequences, except for the underlined C in AON1-4 that was introduced erroneously. OL-1 hRNA/ HOL1-RNA is also referred to herein as QRX-203h (42).

| Name | Sequence | SEQ ID NO: |
|---|---|---|
| AON2 | 5' ACCUUUCUUUGAACCCACAUCU 3' | 10 |
| AON3 | 5' AAUGAUUGCACCUUUGUUUGAACC 3' | 11 |
| AON4 | 5' CGCCCACCAUGAGUCCAAUGA 3' | 12 |
| AON5 | 5' ACUGUCGCUAUGACAACACC 3' | 13 |
| AON6 | 5' UGUACUGUUUCUUCUUCAGC 3' | 14 |
| AON7 | 5' GAUGAAUGGAUGUGUACUGU 3' | 15 |
| AON8 | 5' ucaaguuuaccuacCUCCACCA 3' | 16 |
| AON1-1 | 5' GAACACcuugaaaacaaauuaaga 3' | 17 |
| AON1-2 | 5' ACAUCUUCUGCAAAGAACACcuuga 3' | 18 |
| AON1-3 | 5' UUCUGCAAAGAACACcuugaaaaca 3' | 19 |
| AON1-4 | 5' AUCUUCUGCAAAGCAACACcuugaaaacaaa 3' | 20 |
| QRX-203h (39) | 5' ACCUUUGUUUGAACCCACAUCUUCUGCAAAGAACACCUU 3' | 37 |
| QRX-203h (36) | 5' UUUGUUUGAACCCACAUCUUCUGCAAAGAACACCUU 3' | 38 |
| QRX-203h (33) | 5' GUUUGAACCCACAUCUUCUGCAAAGAACACCUU 3' | 39 |
| QRX-203h (30) | 5' UGAACCCACAUCUUCUGCAAAGAACACCUU 3' | 40 |
| QRX-203h (27) | 5' ACCCACAUCUUCUGCAAAGAACACCUU 3' | 41 |
| AON1-2-1 | 5' CCACAUCUUCUGCAAAGAACACcuug 3' | 47 |
| AON1-4-1 | 5' AUCUUCUGCAAAGAACACcuugaaaacaaa 3' | 48 |
| AON1-4-2 | 5' CCACAUCUUCUGCAAAGAACACcuugaaaacaaa 3' | 49 |

The present invention relates to an antisense oligonucleotide (AON) capable of preventing or reducing exon 17 inclusion into a human APP mRNA, when said mRNA is produced by splicing from an APP transcript in a human cell; characterized in that said AON is capable of binding to and/or is complementary to a region within the 5' part of exon 17 and/or the 3' part of intron 16 of the human APP gene. In a preferred embodiment, the region starts 18 nucleotides upstream of the intron16/exon17 junction (−18) and terminates 40 nucleotides downstream of the intron16/exon17 junction (+40). In a further preferred embodiment, the region spans nucleotides 1 to 40 of exon 17 of the human APP gene (+1 to +40). In an even more preferred embodiment, the region has the sequence of SEQ ID NO: 31. In a particular preferred embodiment, the AON is complementary to a sequence within exon 17, wherein said sequence is selected from the group consisting of SEQ ID NO: 32, 33, 34, and 35. In yet another aspect of the present invention, the region where the AON of the present invention binds to (and/or is complementary to) starts 18 nucleotides upstream of the intron16/exon17 junction (−18) and terminates 18 nucleotides downstream of the intron16/exon17 junction (+18) and has the sequence of SEQ ID NO: 36. In yet another preferred embodiment, the AON has at most 4 or fewer mismatches with its complementary sequence, preferably 3 or fewer, more preferably 2 or fewer, even more preferably 1 or no mismatches. In an even further preferred aspect, the AON is complementary to at least 8 nucleotides, preferably from 8 to 50 nucleotides, more preferably from 12 to 50 nucleotides, within the region. In one aspect, the AON has a length of from 18 to 42, preferably from 22 to 42, more preferably from 27 to 39 nucleotides in length. In another preferred aspect, the AON according to the present invention comprises a nucleotide sequence that is complementary to at least 8 nucleotides within the sequence of SEQ ID NO: 31, and wherein the oligonucleotide comprises the sequence of SEQ ID NO: 9, 17, 18, 19, 20, 28, 29, 37, 38, 39, 40, 41, 47, 48, or 49. In another preferred aspect, the AON of the present invention is an oligoribonucleotide. And in yet another preferred aspect, the invention relates to an AON wherein the internucleosidic linkages of the AON are chemically modified, preferably by comprising phosphorothioate-linkages. In yet another preferred embodiment, the sugar moieties of the AON are lower 2'-O-alkyl, preferably 2'-O-methyl substituted sugar moieties. In a highly preferred aspect, the invention relates to an AON selected from the group consisting of AON1, AON1-1, AON1-2, AON1-3, AON1-4, QRX-203h (42), QRX-203h (39), QRX-203h (36), QRX-203h (33), QRX-203h (30) and QRX-203h (27), each with their respective sequences as disclosed in the sequence listing. In a further preferred aspect, the invention relates to an AON that is an oligoribonucleotide and that has the nucleotide sequence of SEQ ID NO: 29, 37, 38, 39, 40 or 41, and wherein the AON comprises phosphorothioate inter-nucleotide linkages and 2'-OMe sugars.

The present invention also relates to a composition comprising an AON according to the invention, and optionally comprising one or more of a carrier, excipient, stabilizer, transfection agent, diluent, gelling agent or a buffer. Such constituents are well-known by the person skilled in the art. In a particularly preferred aspect, the composition of the present invention is a pharmaceutical composition useful in human therapy.

The invention also relates to a method for preventing or reducing exon 17 inclusion into a human APP mRNA, when said mRNA is produced by splicing from an RNA transcript in a human cell; comprising the steps of providing to a cell, to a tissue, in vitro or ex vivo, or to a living human being comprising such a cell, an AON according to the invention, or a composition according to the invention, under conditions conducive to uptake of such AON by such cell, and allowing splicing to take place. The invention also relates to a method for making an internally truncated human APP protein lacking the region encoded by exon 17 in accordance with the canonical numbering of the exons of the human APP gene, comprising the steps of providing an AON according to the invention, or a composition according to the invention, to a cell that expresses the human APP gene, under conditions conducive to uptake of said AON, allowing the APP gene to be expressed, whereby the APP pre-mRNA is being spliced by the splicing machinery of the cell, thereby producing mRNAs wherein exon 17 is not included, and allowing said mRNA to be translated into the internally truncated protein. In a preferred embodiment, the internally truncated human APP protein is human APP646 (SEQ ID NO: 4). The invention further relates to an isolated human APP646 protein, preferably having the sequence of SEQ ID NO: 4. Such isolated human APP646 protein may also be recombinantly produced on different platforms by methods known to the person skilled in the art.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor models), and/or the free energy of the AON-target exon complex (using RNA structure version 4.5). If a Tm is too high, the oligonucleotide is expected to be less specific. An acceptable Tm and free energy depend on the sequence of the oligonucleotide, the chemistry of the backbone (phosphodiester, phosphorothioate, phosphoramidate, peptide-nucleic acid, etc.), the nature of the sugar moiety (ribose, deoxyribose, substituted ribose, intra-molecular bridge) and chemical modification of the nucleobase. Therefore, the range of Tm can vary widely.

The exon skipping percentage or efficiency may be calculated by determining the concentration of wild-type band amplified, divided by the concentration of the shortened (exon 17-free) band amplified, after a given number of PCR cycles, times 100%, for any given primer set, provided the number of cycles is such that the amplification is still in the exponential phase. Quantification can be performed using the Agilent 2100 Bioanalyzer in combination with DNA1000 kit.

Preferably, an AON according to the invention, which comprises a sequence that is complementary to a nucleotide sequence as shown in SEQ ID NO: 1 is such that the complementary part is at least about 80%, more preferably at least about 90%, still more preferably at least about 95%, most preferably about 100% complementary to the target sequence. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" means that the AONs according to the invention are capable of inducing exon skipping of exon 17. Skipping the targeted exon may conveniently be assessed by PCR/Bioanalyzer, optionally ddPCR. The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide, while the length should not be too long to create problems with manufacturability, purification and/or analytics.

It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatches in an oligonucleotide of 20 nucleotides, and 5 or fewer in an AON of 50 nucleotides.

An AON according to the invention may be longer than the complementary region on the target, having non-base pairing ends or 'overhanging' ends. It is preferred that such 'overhang', which may be on the 5' site or the 3' site or both, should be kept to a minimum, as non-complementary bases at the ends of the AON may reduce the specificity of binding and/or the strength of binding of the AON to the target.

Preferably, the length of the complementary part of the oligonucleotide is the same as the length of the oligonucleotide, meaning there are no 5' or 3' ends of the oligo that do not form a base pair with the target RNA. Thus a preferred length for an oligonucleotide of the invention is 50 nucleotides or less e.g. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 nucleotides. Particularly good results have been obtained with AONs having a length of 20 to 48 nucleotides, more in particular having a length of 27, 30, 33, 36, 39 and 42 nucleotides, all having PS modified backbone and a 2'-OMe chemistry. Such AONs are preferred.

An exon skipping AON according to the invention may contain one or more DNA nucleotides (consequently a RNA "u" residue will be a "t" residue as DNA counterpart), but ideally does not consist solely of DNA nucleotides (due to poor or absent effects). RNA oligonucleotides (including modified RNA) are preferred for exon skipping purposes.

Total knock down of APP RNA has never been tested in humans and may be associated with severe adverse effects. Therefore, exon skipping AONs that do not cause significant, let alone total, APP RNA knock down, are strongly preferred according to the invention. siRNAs aimed at destruction, so-called 'gapmers' invoking RNase H mediated break-down, or any other AONs causing total knockdown of APP are not preferred, according to the invention.

It is preferred that an exon skipping AON of the invention comprises one or more nucleotides that is/are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells.

According to one embodiment of the invention the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages. In accordance with this embodiment, a preferred nucleotide analogue or equivalent comprises a Peptide Nucleic Acid (PNA), having a modified polyamide backbone (Nielsen et al. 1991. Science 254 (5037):1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar. 2005. Chem Commun (Camb) 28:495-497). Since the backbone of a PNA molecule contains no charged phosphate groups, PNA-RNA hybrids are usually more stable than RNA-RNA or RNA-DNA hybrids, respectively (Egholm et al. 1993. Nature 365(6446):566-568).

According to another embodiment of the invention, the backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or di-substituted at the 2', 3' and/or 5' position such as a —OH; —F; substituted or unsubstituted, linear or branched lower (C1-C10) alkyl, alkenyl, alkynyl, alkanyl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, —methoxy, —aminopropoxy; methoxyethoxy; —dimethylaminooxyethoxy; and —dimethylaminoethoxyethoxy. The sugar moiety can be a furanose or derivative thereof, or a deoxyfuranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all internucleosidic linkages in an AON to be modified. For example, some internucleosidic linkages may be unmodified, whereas other internucleosidic linkages are modified. AONs comprising a backbone consisting of one form of (modified) internucleosidic linkages, multiple forms of (modified) internucleosidic linkages, uniformly or non-uniformly distributed along the length of the AON are all encompassed by the present invention. In addition, any modality of backbone modification (uniform, non-uniform, mono-form or pluriform and all permutations thereof) may be combined with any form or of sugar or nucleoside modifications or analogues mentioned below.

An especially preferred backbone for the AONs according to the invention is a uniform (all) phosphorothioate (PS) backbone.

In another embodiment, a nucleotide analogue or equivalent of the invention comprises one or more base modifications or substitutions. Modified bases comprise synthetic and natural bases such as inosine, xanthine, hypoxanthine and other —aza, deaza, —hydroxy, —halo, —thio, thiol, —alkyl, —alkenyl, —alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON of the invention has at least two different types of analogues or equivalents.

According to another embodiment AONs according to the invention comprise a 2'-O (preferably lower) alkyl phosphorothioate AON, such as 2'-O-methyl modified ribose (RNA), 2'-O-methoxyethyl modified ribose, 2'-O-ethyl modified ribose, 2'-O-propyl modified ribose, and/or substituted derivatives of these modifications such as halogenated derivatives.

An effective and preferred AON format according to the invention comprises 2'-O-methyl modified ribose moieties with a phosphorothioate backbone, preferably wherein substantially all ribose moieties are 2'-O-methyl and substantially all internucleosidic linkages are phosphorothioate linkages.

It will also be understood by a skilled person that different AONs can be combined for efficiently skipping of exon 17 of the APP gene. A combination of two AONs may be used in a method of the invention, such as two AONs, three different AONs, four different AONs, or five different AONs targeting the same or different regions of exon 17 and/or intron 16 (FIG. 5), as long as at least one AON is one according to the invention.

An AON can be linked to a moiety that enhances uptake of the AON in cells, preferably brain cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a camelid single domain antigen-binding domain or a scFv.

An exon skipping AON according to the invention may be a naked (gymnotic) AON or in the form of a conjugate, a nanoparticle, or expressed from a vector (vectored AON). The exon skipping AON may be administrated using suitable means known in the art. When the exon skipping AON is a vectored AON, it may for example be provided to an individual or a cell, tissue or organ of said individual in the form of an expression vector wherein the expression vector encodes a transcript comprising said AON. The expression vector is preferably introduced into a cell, tissue, organ or individual via a gene delivery vehicle, such as a viral vector. In a preferred embodiment, there is provided a viral-based expression vector comprising an expression cassette or a transcription cassette that drives expression or transcription of an exon skipping AON as identified herein. Accordingly, the present invention provides a viral vector expressing an exon skipping AON according to the invention when placed under conditions conducive to expression of the exon skipping AON. A cell can be provided with an exon skipping AON capable of interfering with sequences essential for, or at least conducive to, exon 17 inclusion, such that such interference prevents, or at least reduces, exon 17 inclusion into the APP mRNA, for example by plasmid-derived AON expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the mammalian (preferably human) genome of cells may be suitably applied for delivery of an AON as defined herein. Preferred for the current invention are those vectors wherein transcription is driven from Pol-III promoters, and/or wherein transcripts are in the form of fusions with U1 or U7 transcripts, which yield good results for delivering small transcripts. It is within the skill of the artisan to design suitable transcripts. Preferred are Pol-III driven transcripts. Preferably, in the form of a fusion transcript with an U1 or U7 transcript. Such fusions may be generated as described in the art (Gorman et al. 1998; Suter et al. 1999).

One preferred AON expression system is an adenovirus associated virus (AAV)-based vector. Single chain and double chain AAV-based vectors have been developed that can be used for prolonged expression of AON sequences for highly efficient skipping of APP exon 17. A preferred AAV-based vector for instance comprises an expression cassette that is driven by a polymerase III-promoter (Pol III). A preferred Pol III promoter is, for example, a U1, a U6, or a U7 RNA promoter. The invention therefore also provides a viral-based vector, comprising a Pol III-promoter driven expression cassette for expression of an AON of the invention for inducing skipping of APP exon 17.

An AAV vector according to the present invention is a recombinant AAV vector and refers to an AAV vector comprising part of an AAV genome comprising an encoded exon skipping AON according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the present invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the present invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector, respectively.

More preferably, a recombinant AAV vector according to the present invention has tropism for neuronal cells and comprises a capsid protein shell of AAV serotype, including serotypes 1, 2, 5, 7 and 8. The AAV genome or ITRs present in said vector may be derived from the same or a different serotype, such as AAV serotype 2; such vector is referred to as, for example, an AAV 2/8 or AAV 2/9 vector.

More recently, AAV 9 has been reported to possess excellent tropism for neuronal cells in the primate brain (Dayton et al. 2012. Expert Opinion Biol Ther 12(6) 757-766). Hence, the instant invention provides recombinant AAV vectors for delivering AON-expressing constructs to neuronal cells in the brain of AD patients, comprising serotypes 1, 2, 5, 7, 8 and 9, including chimeric rAAV vectors with similar tropism.

In order to improve specificity and reduce toxicity, cell-type specific promoters may be selected that favor, for example, neuronal expression over glial or oligodendrocyte expression.

Various methods of delivery, including intraventricular, intrathecal, intra-parenchymal, intranasal, as well as systemic, including intravenous, subcutaneous methods of delivery are contemplated by the instant invention. Particularly good results have been obtained in clinical studies where patients were dosed with AONs by intrathecal injections. Following intrathecal injection, AONs travel to the brain where they diffuse into various regions of the brain, followed by uptake by a wide variety of cell types.

One method that has been reported to enhance neuronal expression in adults is the use of mannitol to relax the blood-brain barrier to allow vector entry into the CNS (McCarty et al. 2009. Gene Ther 16:1340-1352)

A nucleic acid molecule encoding an exon skipping AON according to the present invention represented by a nucleic acid sequence of choice is preferably inserted between the AAV genome or ITR sequences as identified above, for example an expression construct comprising an expression regulatory element operably linked to a coding sequence and a 3' termination sequence.

"AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art (Chiorini et al. 1999. J Virology 73(2): 1309-1319; U.S. Pat. No. 5,139,941 incorporated herein by reference). The AAV helper functions can be supplied on an AAV helper construct, which may be a plasmid. Introduction of the helper construct into the host cell can occur e.g. by transformation, transfection, or transduction prior to or concurrently with the introduction of the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 (incorporated herein by reference).

Preferably, an AAV genome as present in a recombinant AAV vector according to the present invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

Gymnotic AONs in aqueous solution are readily taken up by most cells in vivo, and usually dissolving the AONs according to the invention in an isotonic (saline) solution will be sufficient to reach the target cells, such as neuronal cell in the human brain. Alternatively, gymnotic AONs of the invention may be formulated using pharmaceutically acceptable excipients, additives, stabilizers and the like. Gymnotic AONs may also be formulated with any of the transfection aids mentioned below.

For intravenous, subcutaneous, intramuscular, intrathecal, intrauterine, cerebrospinal and/or intraventricular administration it is preferred that the solution is an isotonic (saline) solution. Particularly preferred in the invention is the use of an excipient or transfection agents that will aid in delivery of each of the constituents as defined herein to a cell and/or into a cell, preferably a neuronal cell in the human brain. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constitutent as defined herein to a cell, preferably a neuronal cell in the brain. Such excipients have been shown to efficiently deliver an oligonucleotide such as antisense nucleic acids to a wide variety of cultured cells, including neuronal cells. Their high transfection potential is combined with an acceptably low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cf. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a disease or condition associated with Aβ peptide generation.

An exon skipping AON according to the invention could be covalently or non-covalently linked to a targeting ligand specifically designed to facilitate the uptake into the cell (especially a neuronal cell), cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery e.g. to the brain.

It is to be understood that if a composition comprises an additional constituent such as an adjunct compound as later defined herein, each constituent of the composition may be formulated in one single combination or composition or preparation. Depending on their identity, the skilled person will know which type of formulation is the most appropriate for each constituent as defined herein. According to one embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, such as gymnotic AON, a conjugated AON, a nanoparticle, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, excipient, stabilizer, transfection agent, gelling agent, buffer, filler, preservative, adjuvant, solubilizer and/or diluent. Such pharmaceutically acceptable components may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.0001 and 100 mg/kg, preferably from 0.001 and 50 mg/kg, still more preferably between 0.01 and 20 mg/kg.

A preferred exon skipping AON according to the invention is for the treatment of Alzheimer's disease. In all embodiments of the present invention, the term "treatment" is understood to include the prevention and/or delay of the disease or condition, and/or the reduction of the severity of the symptoms. An individual, which may be treated using an exon skipping molecule according to the invention may already have been diagnosed as having AD or being at risk of developing AD. For example, an individual may possess a mutation in exon 17 that gives rise to AD at an earlier age (e.g. as is the case with early onset AD) or in a more severe fashion. Examples thereof are AD caused by the Swedish mutation in APP (K670M/N671L) or the mutation in the AD form called 'hereditary cerebral hemorrhage with amyloidosis-Dutch mutation' (HCHWA-D). Where a patient already suffers from AD, this may be mild, moderate, or severe AD.

The present invention further provides an exon skipping AON according to the invention, such as a gymnotic, conjugated AON, nanoparticle or vectored AON, or a composition comprising the same for use as a medicine for use in treating AD, including all of its subforms, such as early onset AD, familial AD, the Swedish mutation, HCHWA-D, and the like, or—more generally—any condition associated with increased amyloidogenesis in the brain associated with APP processing producing Aβ peptides, fibrils or plaques.

Dosing may be daily, weekly, monthly, quarterly, once per year, depending on the route of administration and the need of the patient or individual at risk.

Depending on the (expected) time of onset of disease, patients having or at risk of developing a disease, disorder or condition caused by or associated with Aβ associated amyloidogenesis, an individual may be treated at any age that seems appropriate to start.

In a preferred embodiment, a viral vector, preferably an AAV vector as described earlier herein, as delivery vehicle for a molecule according to the invention, is administered in a dose ranging from $1\times10^9$-$1\times10^{17}$ virus particles per injection, more preferably from $1\times10^{10}$-$1\times10^{14}$, and most preferably $1\times10^{10}$-$1\times10^{12}$ virus particles per injection.

It will be clear to a person having ordinary skill in the art to which this invention pertains, that the details of treatment will need to be established in accordance with and depending on such factors as the sequence and chemistry of the oligonucleotide(s), the route of administration, the formulation, the dose, the dosing regimen, the format (viral vector or gymnotic oligonucleotide), the age and weight of the patient, the stage of the disease and so forth, which may require further non-clinical and clinical investigation.

The invention further provides a method for preventing, or at least reducing, or slowing down the effects, of Aβ formation and/or accumulation in the mammalian, preferably human, brain, comprising the step of administering to an individual, an exon skipping molecule according to the invention, such as a gymnotic AON or a (viral) vector encoding an AON according to the invention, or a composition according to the invention.

Unless otherwise indicated each embodiment as described herein may be combined with another embodiment as described herein.

In all embodiments of the present invention, the terms "preventing, or at least reducing, exon inclusion" and "exon skipping" are synonymous. In respect of APP, "preventing, or at least reducing, exon inclusion" or "exon skipping" are to be construed as the exclusion of exon 17 (SEQ ID NO: 3, or allelic forms thereof) from the human APP mRNA (see FIG. 5). The term "exon skipping" is herein defined as the induction within a cell of a mature mRNA that does not contain a particular exon that would otherwise (i.e. without exon skipping) be present in the mature mRNA. Exon skipping is achieved by providing a cell, in vitro or in vivo, which expresses the pre-mRNA of said mature mRNA with a molecule capable of interfering with sequences such as, for example, the splice donor or splice acceptor sequence required for allowing the biochemical process of splicing, or with a molecule that is capable of interfering with an exon inclusion signal required for recognition of a stretch of nucleotides as an exon to be included in the mature mRNA; such molecules are herein referred to as "exon skipping molecules". Preferred exon skipping molecules according to the present invention are AONs.

The term "pre-mRNA" refers to a non-processed or partly-processed precursor mRNA that is synthesized from a DNA template in a cell by the cellular transcription machinery.

The term "antisense oligonucleotide" ("AON") refers to a nucleotide sequence which is complementary to a target nucleotide sequence in a pre-mRNA molecule, hnRNA (heterogeneous nuclear RNA) or mRNA molecule, so that it is capable of annealing with its corresponding target sequence.

The term "complementary" as used herein includes "fully complementary" and "substantially complementary", meaning there will usually be a degree of complementarity between the AON and its corresponding target sequence of with 5 or fewer mismatches, preferably 4 or fewer, more preferably 3 or fewer, 2 or fewer, 1 or no mismatches between the complementary part of the AON and the target sequence. The degree of complementarity of the antisense sequence is preferably such that an AON comprising the antisense sequence can anneal (bind) to the target nucleotide sequence in the RNA molecule under physiological conditions, thereby facilitating exon skipping. It is well known to a person having ordinary skill in the art that certain mismatches are more permissible than others, because certain mismatches have less effect on the strength of binding, as expressed in terms of melting temperature or Tm, between AON and target sequence, than others. Certain non-complementary base pairs may form so-called "wobbles" that disrupt the overall binding to a lesser extent than true mismatches. The length of the AON also plays a role in the strength of binding, longer AONs having higher melting temperatures as a rule than shorter AONs, and the G/C content of an oligonucleotide is also a factor that determines the strength of binding, the higher the G/C content the higher the melting temperature for any given length. Certain chemical modifications of the nucleobases or the sugar-phosphate backbone, as contemplated by the present invention, may also influence the strength of binding, such that the degree of complementarity is only one factor to be taken into account when designing an oligonucleotide according to the invention. The presence of a CpG dinucleotide sequence, or a multitude (two or more) of CpGs, in an oligonucleotide is usually associated with an increased immunogenicity of said oligonucleotide (Dorn and Kippenberger. 2008. Mol Ther 10(1):10-20). This increased immunogenicity is undesired since it may induce damage of the tissue to be treated. Whenever possible, the number of CpGs in the AONs according to the invention should be kept to a minimum e.g. only 1 or 2 CpG sequences in the AON (or, ideally, zero CpG sequences).

The terms "adenine", "guanine", "cytosine", "thymine", "uracil" and "hypoxanthine" (the nucleobase in inosine) refer to the nucleobases as such.

The terms adenosine, guanosine, cytidine, thymidine, uridine and inosine, refer to the nucleobases linked to the (desoxy)ribosyl sugar.

The term "nucleoside" refers to the nucleobase linked to the (deoxy)ribosyl sugar.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "include" and all of its tenses and conjugations, is to be read as "include, but is not limited to".

The word "exon skipping molecule" is meant to include gymnotic AONs and vectored AONs, including viral vectors, capable of expressing AONs in a compatible cell.

The word "about" or "approximately" when used in association with a numerical value (e.g. about 10) preferably means that the value may be the given value (of 10) plus or minus 5% of the value.

The sequence information as provided herein should not be so narrowly construed as to require inclusion of erroneously identified bases. The skilled person is capable of identifying such erroneously identified bases and knows how to correct for such errors.

As disclosed herein, the present invention provides several AONs that show a range of skipping efficiencies. While it may be assumed that the highest skipping efficiency will yield the best result in a therapeutic setting, this may not always be the case. The AONs with the best skipping efficiency in the panels tested herein are the fully 'humanized' sequence, with PS and 2'-OMe modifications (coined HOL1-RNA, OL1-hRNA or QRX-203h (42) (SEQ ID NO: 29) in the present application), which is based on the mouse sequence OL1 disclosed in Kumar et al. and U.S. Pat. No. 6,310,468, and its shortened derivatives referred to as QRX-203h (39) (SEQ ID NO: 37), QRX-203h (36) (SEQ ID NO: 38), QRX-203h (33) (SEQ ID NO: 39), QRX-203h (30) (SEQ ID NO: 40) and QRX-203h (27) (SEQ ID NO: 41). QRX-203h (42) and QRX-203h (33) are especially preferred. It will be understood by the person skilled in the art that some experimentation may be required to establish optimal therapeutic effect, while minimizing adverse effects. The most efficient exon skippers may be used in lower concentration than less efficient AONs. This may yield the best balance between therapeutic effect and adverse effect. Alternatively, a less efficient exon skipper may be used at a higher dose. The route of administration, the format (naked, conjugated, complexed, vectored), the exposure time, the chemistry of the AON and the like, will also play a role. All these permutations are open to further optimization that is well within the ambit of a person, or a team of persons, having ordinary skill in the art.

According to another embodiment of the invention, an internally truncated protein is provided with the sequence of APP646 (SEQ ID NO: 4). Further provided is a cell expressing the truncated protein from a cDNA or a minigene construct with intron 16 and/or intron 17, which cell may be a primary cell or an immortalized cell. Such a cell line may be used to screen exon skipping molecules, including antisense ONs, study protein function, processing and/or folding of APP646 and the like. In addition, such cell lines may be used to study the interaction of APP646 with other APP processing fragments, including Aβ.

Further provided are pharmaceutical compositions comprising an oligonucleotide according to the invention.

EXAMPLES

Example 1. Design and Testing AONs for Exon 17 Skipping within Human APP Pre-mRNA A number of AONs that are complementary to the boundary of intron 16 and exon 17, within exon 17 and at the boundary of exon 17 and intron 17 were known in the art: OL1-DNA and OL3 (DNA oligo's), and hAPPEx16_1 to 6. The inventors of the present invention sought for improved AONs partly based on these known AONs and partly based on new insights. Several fully phosphorothioate and 2'-O-methyl modified AONs were thus designed for exon skipping and screened for efficiency. The new AONs were designed to bind the region spanning exon 17 as well as regions that overlap the intron 16/exon 17 and exon 17/intron 17 junctions (FIG. 5). The human neuroblastoma cell line SK-N-SH was reverse nucleofected in 6-well plates (at 2 µg final AON and a seeding density of 300,000 cells per well) and harvested after 24 or 48 hours. Skip-positive oligonucleotides were further tested at various concentrations and using different transfection reagents. Polymerase chain reaction (PCR) using primers that bind exon 16 and 18 was used to identify the relevant APP transcripts. These products were also quantified by reverse transcription quantitative real-time PCR (RT-PCR). APP protein was measured by an enzyme-linked immunosorbent assay (ELISA) and by immunoblotting. The SK-N-SH cell line, being of neuroblastoma origin predominantly expresses the APP695 isoform.

Cells and Culture Conditions:

SK-N-SH (ATCC® HTB-11™) human dopaminergic neuroblastoma cells, as well as mouse fibroblasts (C57BL/6J) were used for mRNA and endogenous expression analysis. COS7 cells (ATCC® CRL-1651™) were used for heterologous protein expression analysis. SK-N-SH cells were cultured in Eagle's minimum essential medium (M5650, Sigma Aldrich) supplemented with 10% FBS (Ser. No. 10/270,106, ThermoFischer), 1 mM sodium pyruvate (Ser. No. 11/360,070, ThermoFischer) and 2 mM L-alanyl-L-glutamine (35050061, ThermoFischer). Mouse fibroblasts were cultured in DMEM (ThermoFischer, 41966029) supplemented with 15% FBS and 1× antibiotic-antimicotic (Ser. No. 15/240,062, ThermoFischer). COS7 cells were cultured in DMEM supplemented with 10% FBS. Cells were incubated at 37° C. with $CO_2$ levels maintained at 5% and a relative humidity of 80-90%.

AONs and Transfection:

Phosphorothiolated and 2'-O-methyl modified AONs (AON) (IDT and Eurogentec) targeting sequence motifs within intron 16 and exon 17 of the human amyloid precursor protein (APP) gene were designed and screened for skipping exon 17. Transfection was performed with polyethylenimine "Max" (Polysciences, Inc. 24765-2) at a DNA: transfection reagent ratio of 1:3 (w/w) or TurboFect (Dharmacon™, R05531) at a DNA: transfection reagent ratio of 1:2 (w/v). Reverse transfection was used to deliver AONs to cells which were 80-90% confluent prior to transfection. Briefly, 1-3 µg of AON was diluted in 200 µl Opti-MEM® (ThermoFischer, 11058-021) and corresponding amounts of transfection reagent added. After mixed thoroughly by pipetting, the mix was incubated at room temperature for 20-30 minutes. 200 µl of the AON/transfection reagent mix was evenly layered at the bottom of the well of a 6-well plate and 3-4×10$^5$ cells seeded in a total volume of 2 mL. Cells were incubated for 24 hours prior to harvest and analysis or media refreshed 6 hours post transfection and incubated for a further 42 hours before mRNA isolation and PCR analysis.

mRNA Assays:

mRNA was isolated using the ReliaPrep™ RNA cell Miniprep System (Promega) according to the manufacturer's instructions. RNA concentration was adjusted to 100 ng/µl in nuclease-free water and cDNA synthesis performed with random hexamers and anchored oligo dT primers using Verso™ cDNA synthesis kit (Thermo Scientific) or Maxima First Strand cDNA Synthesis Kit (K1671, ThermoFischer) with 500 ng total RNA. A 30 cycle PCR was performed with 2 µL of the cDNA synthesis product using primers flanking exon 17 of APP gene ($F_{exon16}$, SEQ ID NO: 7; $R_{exon18}$, SEQ ID NO: 8). The resulting products were analyzed using 1 µL PCR product on an Agilent 2100 Bioanalyzer (Agilent Technologies) or traditional 2% agarose gel.

Droplet Digital PCR (ddPCR) was used for absolute quantification of transcripts lacking exon 17 after AON treatment. To measure percentage skip in total APP transcripts, primer pairs were designed (SEQ ID NO: 7 and 8) that bind on exons 16 and 18 of APP. After cDNA synthesis using random hexamer and oligodT primer mixes, droplet PCR amplification was performed with the flanking gene-specific primers and a dsDNA binding dye. Transcripts missing exon 17 result in a PCR product that is 147 nucleotides shorter than transcripts including exon 17. Positive droplets with longer amplicons (unskipped APP) have a higher fluorescence amplitude and can be distinguished from positive droplets containing shorter amplicons (skipped APP) which have lower fluorescence amplitude. By using Poisson regression to analyze fluorescence data, the initial DNA input in thousands of droplets allows the absolute quantification of APP transcripts with and without exon 17. The cDNA synthesis mix contained 4 µl 5×cDNA synthesis buffer, 2 µl dNTP mix, 0.25/0.75 µl oligodT/random hexamer (1:3), 1 µl RT Enhancer, 1 µl Verso Enzyme mix and 11 µl RNA (50 ng). The PCR was performed as follows: 5 min hold at 95° C., 30 cycles with 30 sec 95° C. denaturing, 30 sec 60° C. annealing and 35 sec 72° C. extending, followed by a final extension of 7 min at 72° C. and a final hold at 16° C. Results are shown in FIGS. 6 and 7. The best exon skipping was seen with AON1, AON1-2, and (best of all in this initial experiment) HOL1-RNA (i.e. the humanized RNA PS 2'-OMe version of the DNA oligo of U.S. Pat. No. 6,310,048, also referred to in the present invention as OL1-hRNA or QRX-203h (42)).

Example 2. Testing Additional and Further Improved AONs for Exon 17 Skipping

Figure 8:
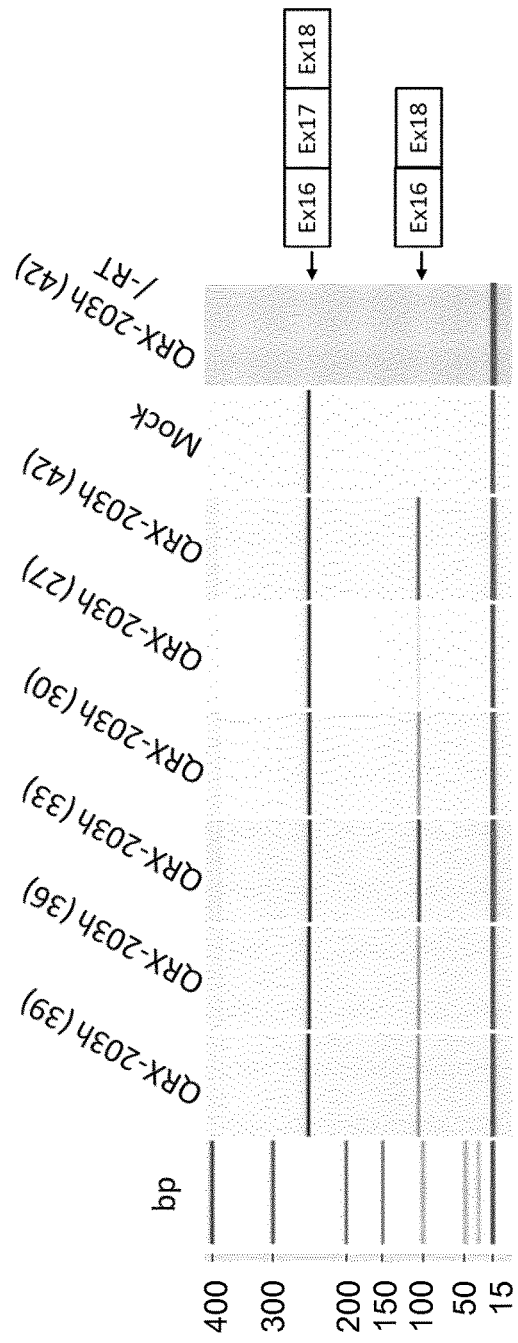
FIG. 8: AON mediated exon 17 skipping within the human APP pre-mRNA in human SK-N-SH cells, using five AONs based on QRX-203h (42) with a 3-nucleotide step shortening from the 5' end of QRX-203h (42), as outlined in Example 2.

The inventors of the present invention reasons that a shorter version of the QRX-203h (42) AON would be preferred for therapeutic settings, costs and handling. Hence, additional AONs were designed that were shortened at the 5' end of QRX-203h (42) by steps of 3. This does not limit the invention in any way, because shortening may also been done by steps of 1, 2, 4 or more nucleotides. This resulted in 5 additional AONs that were also fully 2'-O-methyl modified and comprising all phosphorothioate (PS) linkages. The results with QRX-203h (39) (SEQ ID NO; 37), QRX-203h (36) (SEQ ID NO: 38), QRX-203h (33) (SEQ ID NO: 39), QRX-203h (30) (SEQ ID NO: 40) and QRX-203h (27) (SEQ ID NO: 41) and QRX-203h (42) now acting as a positive control, are shown in FIG. 8. It is clear that the use of all shortened versions of QRX-203h (42) result in efficient exon 17 skipping, with QRX-203h (33) slightly outperforming the others and QRX-203h (27) being the least efficient.

Example 3. Testing Corresponding AONs for Exon 17 Skipping in Mouse Fibroblasts

Figure 9:
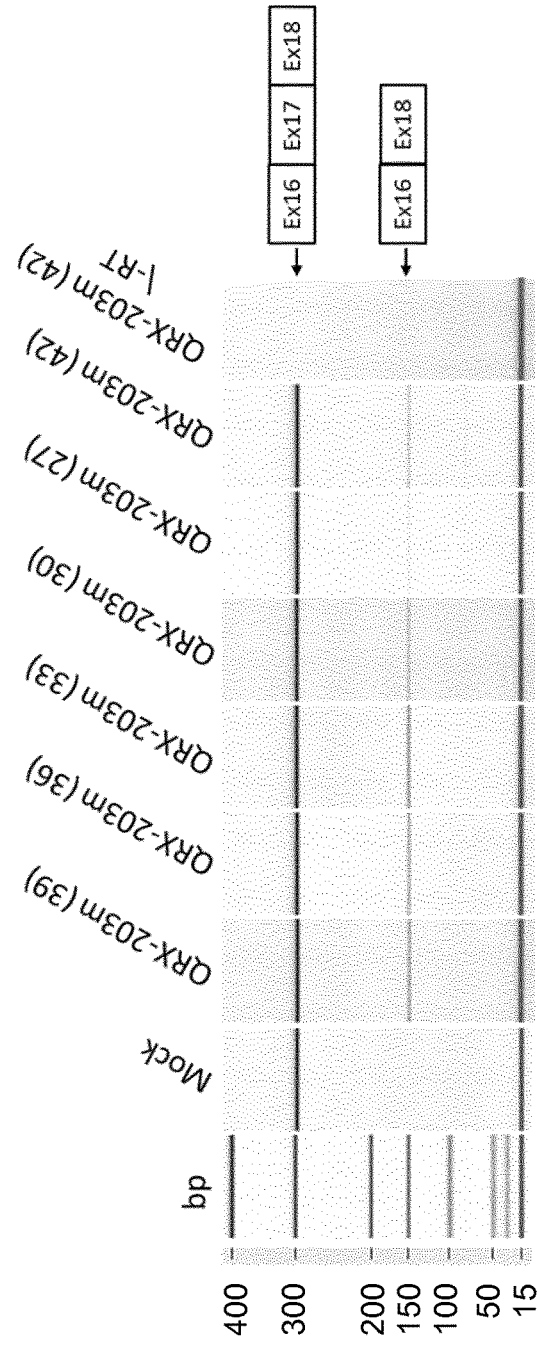
FIG. 9: AON mediated exon 17 skipping within the mouse APP pre-mRNA in mouse fibroblasts, using five additional AONs based on OL-1 RNA mouse (also a 42-mer) with a 3-nucleotide step shortening from the 5' end, as outlined in Example 3.

The experiment of Example 2 was repeated in mouse fibroblasts using AONs that hybridize to the intron 16 and exon 17 sequences of the mouse APP pre-mRNA. These AONs, that have slightly different sequences as compared to their human counterparts, are referred to as QRX-203m (39) (SEQ ID NO; 42), QRX-203m (36) (SEQ ID NO: 43), QRX-203m (33) (SEQ ID NO: 44), QRX-203m (30) (SEQ ID NO: 45) and QRX-203m (27) (SEQ ID NO: 46). QRX-203m (42) (also referred to herein as OL-1 RNA mouse; SEQ ID NO: 28) was taken along as positive control. Results are provided in FIG. 9 and show that proper exon 17 skipping efficiency could also be achieved in mouse cells, with again QRX-203m (33), the 33-mer of SEQ ID NO: 44) outperforming the others.

Example 4. Dose Dependency of QRX-203h (33) and QRX-203h (42)

Figure 10:
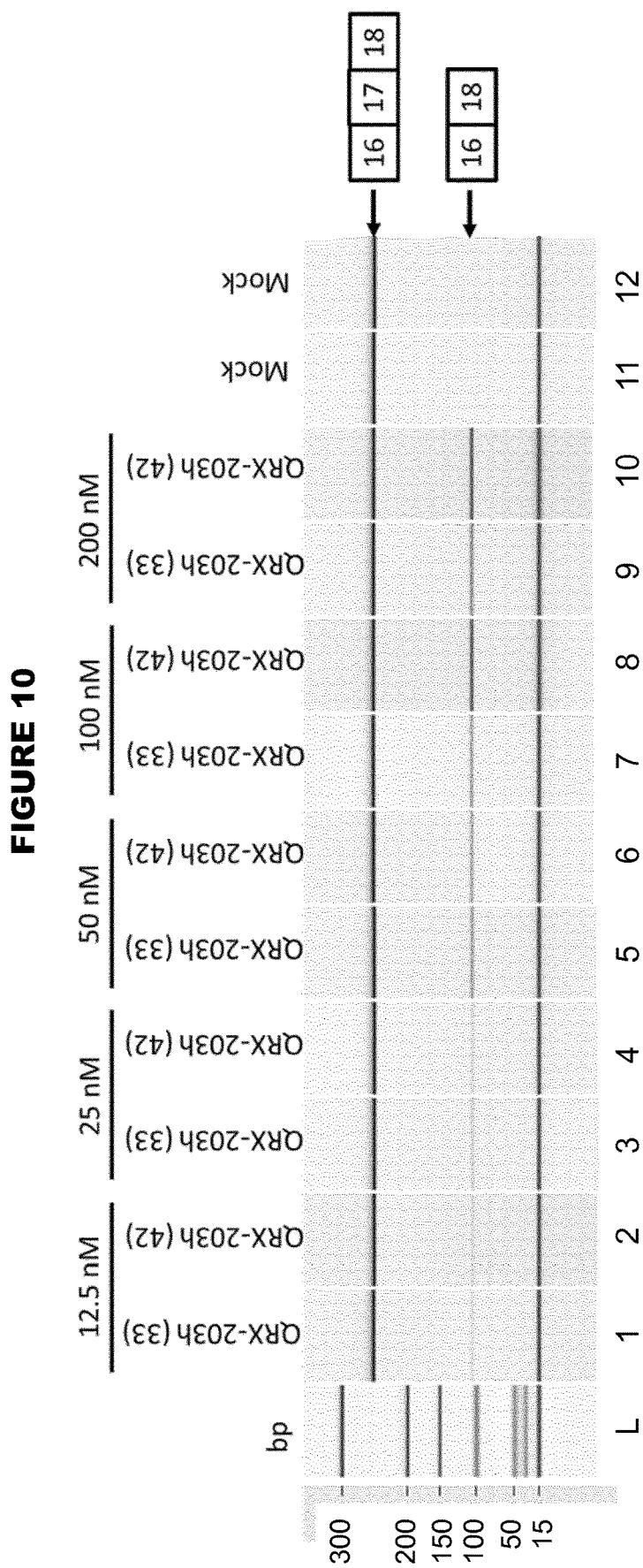
FIG. 10: Dose-dependent AON mediated exon 17 skipping within the human APP pre-mRNA in human SK-N-SH cells, using five increasing concentrations of QRX-203h (33) and QRX-203h (42), as outlined in Example 4.

Because the 33-mer antisense oligonucleotides (AONs; human version: QRX-203h (33); mouse version: QRX-203m (33)) performed generally as good as the QRX-203h (42) AON, it was decided to compare these two AONs in a dose-dependency experiment. Using a similar setup as described in Example 2, five different concentrations were tested: 12.5, 25, 50, 100 and 200 nM. The results are provided in FIG. 10, that shows that there is dose-dependency and that with all five concentrations exon 17 skipping was detected. In this particular experiment, using 100 and 200 nM AON the longer version QRX-203h (42) performed best.

Example 5. Expression of APP646

Next, it was evaluated if the "non-natural" isoform of APP lacking exon 17 (APP-Δ17, also referred to as APP646) can in fact be expressed and whether it is soluble in a physiological context using both heterologous and endogenous expression systems. This is important, because skipping exon 17 may be feasible on an RNA level, but the resulting protein still needs to be actively expressed after exon 17 skipping. For heterologous expression, COS7 cells were transiently transfected with plasmids constitutively expressing APP-WT or APP-Δ17 for 24 hours. The expression plasmids were generated from cDNA and constructed using general knowledge and tools known to the person skilled in the art of molecular biology.

Figure 11:
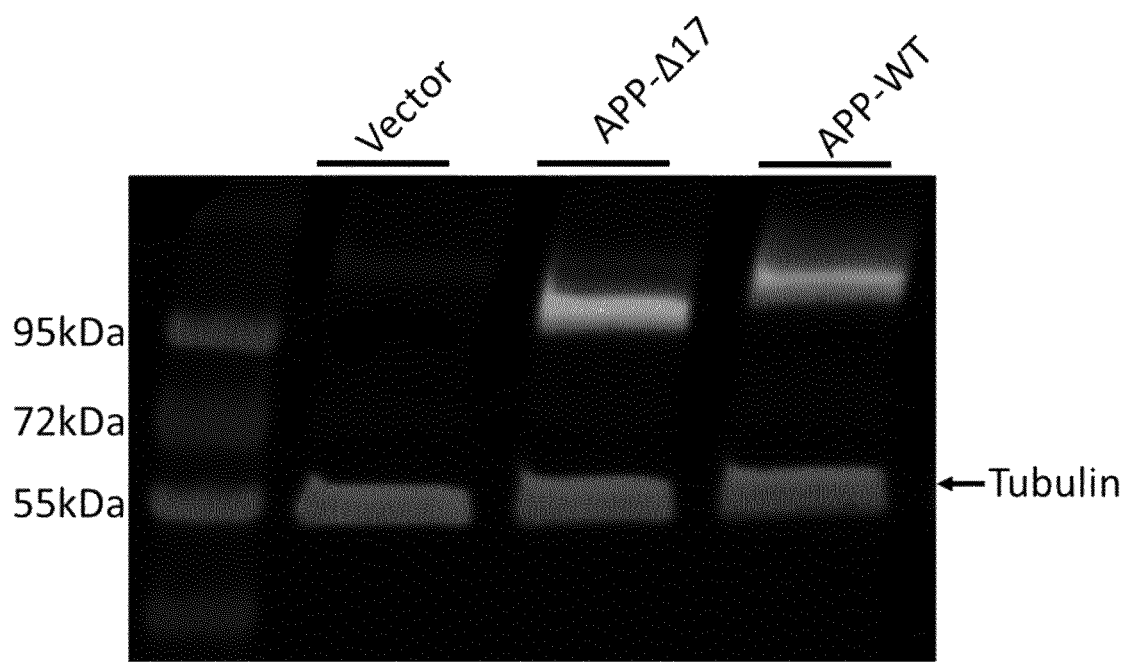
FIG. 11: Heterologous expression of human APP-Δ17 (exon 17 skipped, APP646) and APP695 (full length) in COS7 cells.

The Western blots were performed as follows: Total protein was extracted using M-PER mammalian protein extraction reagent (78501, ThermoFischer) supplemented with cOmplete™ Mini Protease Inhibitor cocktail (11697498001, Roche) 24 hr transfection with oligo's or plasmids expressing corresponding APP variants. Lysates were centrifuged for 25 min at 14,000 rpm in a cooled table top centrifuge and supernatant transferred to new pre-chilled 1.5-ml tubes. Protein concentration was measured with the BCA relative quantification method (23225, ThermoFischer). Protein samples were mixed 4:1 with 4× concentrated reducing loading buffer and boiled for 10 min at 95° C. Samples were resolved on 4-20% Mini-PROTEAN® TGX™ gels (4561096, Bio-Rad) and transferred onto 0.2 µm pore-size nitrocellulose membrane. Membranes were blocked overnight with Odyssey® Blocking Buffer (LI 927-40000, LI-COR). A rabbit anti-APP polyclonal antibody (171610, Merck-Millipore) that recognizes an epitope on the C-terminus of APP was used to detect both wild type and APP-Δ17. As a loading control, either β-actin or Tubulin is checked. IRDye secondary antibodies (800CW Goat anti-Rabbit and 680RD Goat anti-mouse, LI-COR) were used and blots scanned using the Odyssey infrared imaging system. As is apparent from FIG. 11, heterologous APP-Δ17 is expressed and soluble in COS7 cells.

Figure 12A:
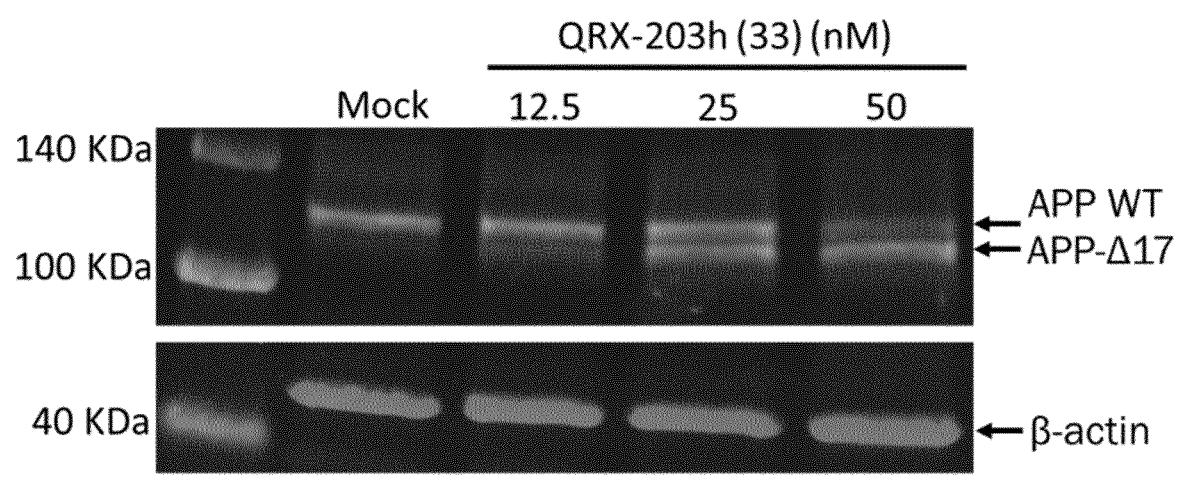
FIG. 12: (A) Expression of wt APP and APP646 (APP-Δ17, from which exon 17 is skipped) in SK-N-SH cells 24 hours after transfection with QRX-203h (33); (B) Wild-type mouse fibroblasts 24 hours after transfection with QRX-203m (33); (C) SK-N-SH cells 24 hours after transfection with QRX-203h (33) or QRX-203h (42); (D) Wild-type mouse fibroblast 24 hours after transfection with QRX-203m (33) or QRX-203m (42). Cells were transfected with various concentrations of QRX-203 (33) or QRX-203 (42) as depicted and cell lysates probed with an antibody that recognizes an epitope on the C-terminus of APP.
Figure 12B:
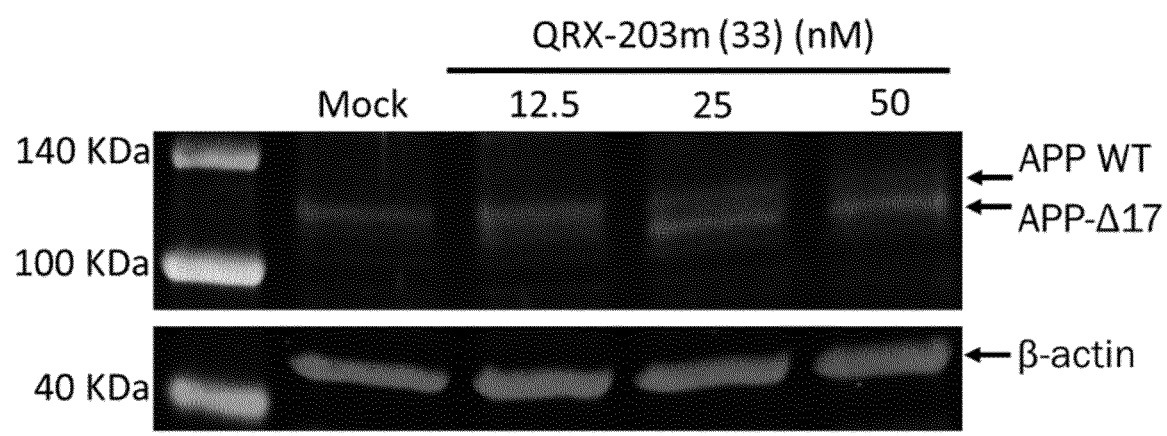

Then, it was tested whether also endogenous protein levels of the wild type and exon 17 skipped protein could be detected upon treatment with AONs. For this, both the mouse and human versions of the 33-mer and 42-mer AONs were tested in mouse fibroblasts and human SK-N-SH cells respectively, using different combinations. The results of these experiments are shown in FIG. 12. It is evident that the AONs of the present invention are able to provide a very abundant exon 17 skipping of endogenous mouse and human APP in cells, which is further stimulated when the concentration of the oligo is increased, even to levels wherein the wt full length protein starts to decrease in amount.

Example 6. Exon 17 Skipping in the Eye of Mice Treated with QRX-203m (42)

Age related macular degeneration (AMD) is the most common cause of irreversible blindness and is characterized by the degeneration of the macula (Ratnapriya and Chew. 2013. Clin Genet 84(2):160-166; Jager et al. 2008. N Engl J Med 358:2606-2617). While the pathophysiology of AMD is complicated and no single known cause has been described, there are several genetic and epigenetic risk factors (Fritzsche et al. 2013. Nat Genet 45(4):433-9, 439e1-2; Chakravarthy et al. 2010. BMC Ophthalmology 10:31; Thornton et al. 2005. Eye 19:935-944). Pathologically, several studies have linked abnormal accumulation of amyloid beta (Aβ) in the macula of the eye (Ohno-Matsui. 2011. Prog Retin Eye Res 30(4):217-38), thus prompting the reference of AMD as the "dementia of the eye." Similar to AD, attempts have been made to remove amyloid plaques from the eye with the use of monoclonal antibodies (Ding et al. 2008. Vision Res 48(3): 339-345).

With this background, the inventors of the present invention reasoned that the APP exon skipping strategy using the AONs of the present invention as disclosed herein could be used to prevent the inclusion of Aβ in the mature APP in retinal ganglion and retinal pigment epithelium cells. For this, wild type C57Bl/6J mice were used to investigate if QRX-203 leads to APP exon 17 skip in the retina of the eye. Prior to intravitreal injection of vehicle (PBS) or QRX-203m (42), 12 mice were anesthesized with ketamine hydrochloride and both eyes dilated with tropicamide (1%)+phenylephrine (2.5%) solution. Mice were divided into a control group (PBS treatment, n=6) and a test group (100 µg QRX-203m (42) treatment, n=6). Mice were injected with 1 µl PBS (control) or 100 µg QRX-203m (42) in 1 µl PBS (test) and recovered using antsedan. Mice were sacrificed 48 hrs (n=3 from each cohort) or 7 days (n=3 from each cohort) post injection and the retina surgically removed. Total RNA was isolated using the ReliaPrep™ RNA cell Miniprep System (Promega) according to the manufacturer's instructions. RNA concentration was adjusted to 100 ng/µl in nuclease-free water and cDNA synthesis performed with oligo dT primers using Verso First Strand cDNA Synthesis Kit (AB1453A, ThermoFischer) with 500 ng total RNA. A 35 cycle PCR was performed with 2 µL of the cDNA synthesis product using primers flanking exon 17 of APP gene using m444 forward primer: 5'-TCTGGGC TGAC-AAACATCAA-3' (SEQ ID NO: 50) and m445 reverse primer: 5'-TTCTGCTGCATCTTGGAGAG-3' (SEQ ID NO: 51). The resulting products were analyzed using 1 µL PCR product on an Agilent 2100 Bioanalyzer (Agilent Technologies.)

Figure 13:
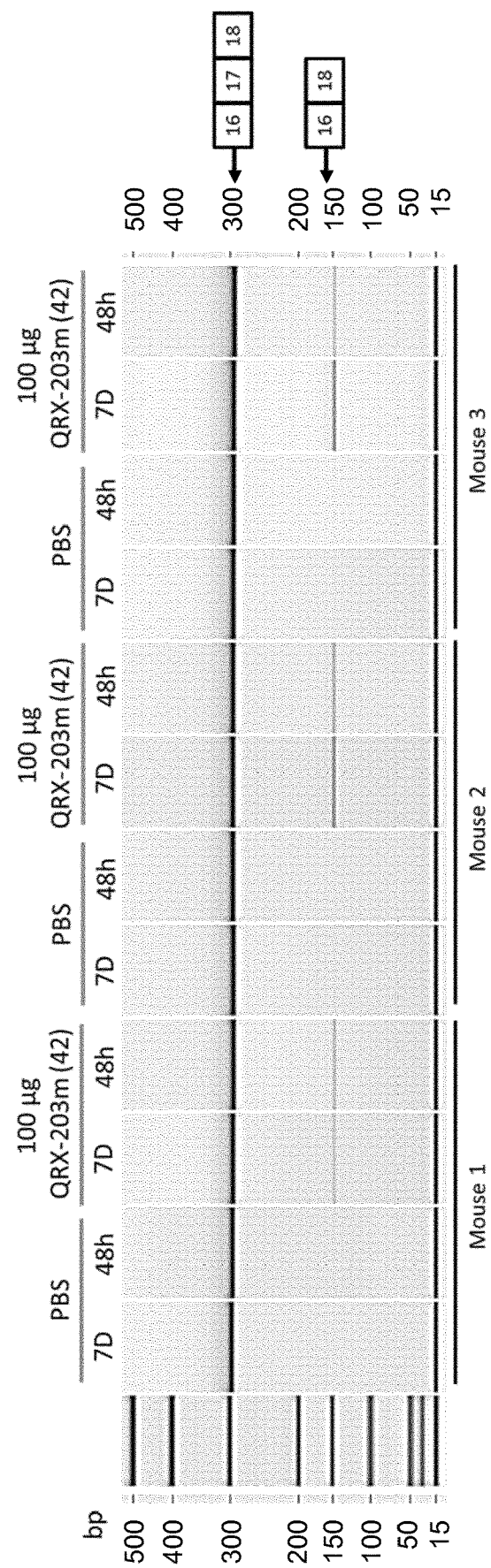
FIG. 13: Exon 17 skipping in the retina of eyes in mice after injection with QRX-203m (42).

The results given in FIG. 13 show that APP exon 17 is skipped in the retinal tissues from QRX-203m (42) treated mice in both the 48 hrs and 7 days cohorts. Additionally, there is more skipped product in the 7 days cohort implying that QRX-203m (42) accumulates and persists in the relevant tissues exerting its effect. These results provide preliminary proof of concept that skipping of APP exon 17 in the eye may be an effective way of reducing or preventing the accumulation of Aβ plaques in the macula.

The invention claimed is:

1. An antisense oligonucleotide (AON) capable of preventing or reducing exon 17 inclusion into a human APP mRNA when the mRNA is produced by splicing from an APP transcript in a human cell, wherein the AON is 12, 13, 14, 15, 16, 17, 18, 19, 20, 21, 22, 23, 24, 25, 26, 27, 28, 29, 30, 31, 32, 33, or 34 nucleotides in length and comprises a sequence that is 100% complementary to the sequence of SEQ ID NO: 32.

2. The AON of claim 1, wherein the AON has a length of from 18 to 34 nucleotides.

3. The AON of claim 1, wherein the AON comprises a nucleotide sequence that is complementary to at least 8 nucleotides within the sequence of SEQ ID NO: 31, and wherein the AON comprises the sequence of SEQ ID NO: 9, 4-7, 18, 19 39, 40, 41, 47, 48, or 49.

4. The AON of claim 1, wherein the AON is an oligoribonucleotide.

5. The AON of claim 1, wherein the internucleosidic linkages of the AON are phosphorothioate-linkages.

6. The AON of claim 1, wherein the AON comprises a 2'-O-alkyl substituted sugar moiety.

7. An antisense oligonucleotide (AON) consisting of a nucleotide sequence selected from the group consisting of SEQ ID NO: 9, 18, 19, 39, 40, 41, 47, 48, and 49.

8. An antisense oligonucleotide (AON) comprising the nucleotide sequence of SEQ ID NO: 29, 37, 38, 39, 40 or 41, wherein the AON is an oligoribonucleotide, comprises phosphorothioate inter-nucleotide linkages, and comprises 2'-O-methyl or 2'-O-methoxyethyl sugars.

9. A pharmaceutical composition comprising the AON of claim 1 and one or more of a carrier, excipient, stabilizer, transfection agent, diluent, gelling agent or a buffer.

10. A method for preventing or reducing exon 17 inclusion into a human APP mRNA when the mRNA is produced by splicing from an RNA transcript in a human cell, the method comprising providing to (i) the cell, in vitro or ex vivo, (ii) a tissue comprising the cell, in vitro or ex vivo, or (iii) a living human being comprising the cell, the AON of claim 1, under conditions conducive to uptake of the AON by the cell, and allowing splicing to take place.

11. A method for making an internally truncated human APP protein lacking the region encoded by exon 17, the method comprising the steps of providing the antisense oligonucleotide (AON) of claim 1 to a cell that expresses the human APP gene, under conditions conducive to uptake of the AON, allowing the APP gene to be expressed, whereby the APP pre-mRNA is spliced by the splicing machinery of the cell, thereby producing mRNAs wherein exon 17 is not included, and allowing the mRNA to be translated into the internally truncated protein.

12. The method of claim 11, wherein the internally truncated human APP protein is human APP646 (SEQ ID NO: 4).

13. The AON of claim 6, wherein the 2'-O-alkyl substituted sugar moiety is a 2'-O-methyl substituted sugar moiety.

14. The AON of claim 6, wherein the 2'O-alkyl substituted sugar moiety is a 2'-O-methoxyethyl substituted sugar moiety.

* * * * *

SEQUENCE LISTING

```
<160> NUMBER OF SEQ ID NOS: 73

<210> SEQ ID NO 1
<211> LENGTH: 251
<212> TYPE: RNA
<213> ORGANISM: Homo sapiens
<220> FEATURE:
<223> OTHER INFORMATION: intron 16 - exon 17 - intron 17

<400> SEQUENCE: 1
auuauauugc auuuagaaau uaaaauucuu uuucuuaauu uguuuucaag guguucuuug     60
cagaagaugu ggguucaaac aaaggugcaa ucauuggacu caugguggggc gguguuguca    120 uagcgacagu gaucgucauc accuggguga ugcugaagaa gaaacaguac acauccauuc    180
aucauggugu ggguggaggua gguaaacuug acugcauguu uccaagugggg aauuaagacu   240 augagagaau u                                                          251

<210> SEQ ID NO 2
<211> LENGTH: 14
<212> TYPE: PRT
<213> ORGANISM: Homo sapiens
<220> FEATURE:
<223> OTHER INFORMATION: C-terminal portion of the Abeta peptide

<400> SEQUENCE: 2

Gly Ala Ile Ile Gly Leu Met Val Gly Gly Val Val Ile Ala
1               5                   10

<210> SEQ ID NO 3
<211> LENGTH: 147
<212> TYPE: RNA
<213> ORGANISM: Homo sapiens
<220> FEATURE:
<223> OTHER INFORMATION: Exon 17

<400> SEQUENCE: 3
guguucuuug cagaagaugu ggguucaaac aaaggugcaa ucauuggacu caugguggggc   60 gguguuguca uagcgacagu gaucgucauc accuggguga ugcugaagaa gaaacaguac   120
acauccauuc aucauggugu gguggag                                         147

<210> SEQ ID NO 4
<211> LENGTH: 646
<212> TYPE: PRT
<213> ORGANISM: Artificial Sequence
<220> FEATURE:
<223> OTHER INFORMATION: Description of Artificial Sequence: Synthetic
      APP646 sequence

<400> SEQUENCE: 4
```

-continued

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                 20                  25                  30

Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
 50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415
```

-continued

```
Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Asp Ala Ala Val Thr Pro Glu Glu Arg His
    610                 615                 620

Leu Ser Lys Met Gln Gln Asn Gly Tyr Glu Asn Pro Thr Tyr Lys Phe
625                 630                 635                 640

Phe Glu Gln Met Gln Asn
                645

<210> SEQ ID NO 5
<211> LENGTH: 695
<212> TYPE: PRT
<213> ORGANISM: Homo sapiens
<220> FEATURE:
<223> OTHER INFORMATION: APP695

<400> SEQUENCE: 5

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125
```

```
Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
            405                 410                 415

Asn Met Leu Lys Lys Tyr Val Arg Ala Glu Gln Lys Asp Arg Gln His
        420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
        500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
```

```
                545                 550                 555                 560
Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 6
<211> LENGTH: 49
<212> TYPE: PRT
<213> ORGANISM: Homo sapiens
<220> FEATURE:
<223> OTHER INFORMATION: Skipped sequence (aa.608-656 of SEQ ID NO: 5)

<400> SEQUENCE: 6

Val Phe Phe Ala Glu Asp Val Gly Ser Asn Lys Gly Ala Ile Ile Gly
1               5                   10                  15

Leu Met Val Gly Gly Val Val Ile Ala Thr Val Ile Val Ile Thr Leu
            20                  25                  30

Val Met Leu Lys Lys Lys Gln Tyr Thr Ser Ile His His Gly Val Val
        35                  40                  45

Glu

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Forward primer

<400> SEQUENCE: 7
tccgacatga ctcaggatat ga                                        22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer

<400> SEQUENCE: 8
tagccgttct gctgcatctt                                           20

<210> SEQ ID NO 9
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      Antisense oligonucleotide AON1

<400> SEQUENCE: 9
uucugcaaag aacaccuuga aa                                              22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      Antisense oligonucleotide AON2

<400> SEQUENCE: 10
accuuucuuu gaacccacau cu                                              22

<210> SEQ ID NO 11
<211> LENGTH: 24
<212> TYPE: RNA
<213> ORGANISM: Artificial Sequence
<220> FEATURE:
<223> OTHER INFORMATION: Description of Artificial Sequence: Synthetic
      Antisense oligonucleotide AON3

<400> SEQUENCE: 11
aaugauugca ccuuuguuug aacc                                            24

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      Antisense oligonucleotide AON4

<400> SEQUENCE: 12
cgcccaccau gaguccaaug a                                               21

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      Antisense oligonucleotide AON5

<400> SEQUENCE: 13
acugucgcua ugacaacacc                                                 20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      Antisense oligonucleotide AON6

<400> SEQUENCE: 14
uguacuguuu cuucuucagc                                                 20

<210> SEQ ID NO 15
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      Antisense oligonucleotide AON7

<400> SEQUENCE: 15
gaugaaugga uguguacugu                                                     20

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      Antisense oligonucleotide AON8

<400> SEQUENCE: 16
ucaaguuuac cuaccuccac ca                                                  22

<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      Antisense oligonucleotide AON1-1

<400> SEQUENCE: 17
gaacaccuug aaaacaaauu aaga                                                24

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      Antisense oligonucleotide AON1-2

<400> SEQUENCE: 18
acaucuucug caaagaacac cuuga                                               25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      Antisense oligonucleotide AON1-3

<400> SEQUENCE: 19
uucugcaaag aacaccuuga aaaca                                               25

<210> SEQ ID NO 20
<211> LENGTH: 31
<212> TYPE: RNA
<213> ORGANISM: Artificial Sequence
<220> FEATURE:
<223> OTHER INFORMATION: Description of Artificial Sequence: Synthetic
      Antisense oligonucleotide AON1-4

<400> SEQUENCE: 20
aucuucugca aagcaacacc uugaaaacaa a                                        31

<210> SEQ ID NO 21
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      hAPPEx16_1 (LUMC1) sequence

<400> SEQUENCE: 21
accaugaguc caaugauugc                                                   20

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
      hAPPEx16_2 (LUMC2) sequence

<400> SEQUENCE: 22
ucaccaaggu gaugacgauc                                                   20

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      hAPPEx16_3 (LUMC3) sequence

<400> SEQUENCE: 23
caccaugaug aauggaugug uac                                               23

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      hAPPEx16_4 (LUMC4) sequence

<400> SEQUENCE: 24
guuugaaccc acaucuucug c                                                 21

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      hAPPEx16_5 (LUMC5) sequence

<400> SEQUENCE: 25
cuguuucuuc uucagcauca cc                                                22

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      hAPPEx16_6 (LUMC6) sequence

<400> SEQUENCE: 26
cuaccuccac cacaccauga uga                                               23

<210> SEQ ID NO 27
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      OL-1 DNA mouse oligonucleotide
<220> FEATURE:
<223> OTHER INFORMATION: Description of Combined DNA/RNA Molecule:
      Synthetic OL-1 DNA mouse oligonucleotide

<400> SEQUENCE: 27
ggcgcctttg ttcgaaccca cacttcagc aaagaacacc ag                           42

<210> SEQ ID NO 28
<211> LENGTH: 42
<212> TYPE: RNA
<213> ORGANISM: Artificial Sequence
<220> FEATURE:
<223> OTHER INFORMATION: Description of Artificial Sequence: Synthetic
      OL-1 RNA mouse sequence

<400> SEQUENCE: 28
ggcgccuuug uucgacccca caucuucagc aaagaacacc ag                          42

<210> SEQ ID NO 29
<211> LENGTH: 42
<212> TYPE: RNA
<213> ORGANISM: Artificial Sequence
<220> FEATURE:
<223> OTHER INFORMATION: Description of Artificial Sequence: Synthetic
      OL-1 hRNA / HOL1-RNA sequence

<400> SEQUENCE: 29
ugcaccuuug uuugaaccca caucuucugc aaagaacacc uu                          42

<210> SEQ ID NO 30
<211> LENGTH: 14
<212> TYPE: RNA
<213> ORGANISM: Artificial Sequence
<220> FEATURE:
<223> OTHER INFORMATION: Description of Artificial Sequence: Synthetic
      OL-3 sequence

<400> SEQUENCE: 30
aacccacauc uuca                                                         14

<210> SEQ ID NO 31
<211> LENGTH: 57
<212> TYPE: RNA
<213> ORGANISM: Homo sapiens
<220> FEATURE:
<223> OTHER INFORMATION: Part of exon 17 of the human APP gene

<400> SEQUENCE: 31
ucuuaauuug uuuucaaggu guucuuugca gaagaugugg guucaaacaa aggugca          57

<210> SEQ ID NO 32
<211> LENGTH: 15
<212> TYPE: RNA
<213> ORGANISM: Homo sapiens
<220> FEATURE:
<223> OTHER INFORMATION: Part of exon 17 of the human APP gene

<400> SEQUENCE: 32
guguucuuug cagaa                                                        15

<210> SEQ ID NO 33
<211> LENGTH: 16
<212> TYPE: RNA
<213> ORGANISM: Homo sapiens
<220> FEATURE:
```

```
<223> OTHER INFORMATION: Part of exon 17 of the human APP gene

<400> SEQUENCE: 33
guguucuuug cagaag                                                     16

<210> SEQ ID NO 34
<211> LENGTH: 17
<212> TYPE: RNA
<213> ORGANISM: Homo sapiens
<220> FEATURE:
<223> OTHER INFORMATION: Part of exon 17 of the human APP gene

<400> SEQUENCE: 34
guguucuuug cagaaga                                                    17

<210> SEQ ID NO 35
<211> LENGTH: 18
<212> TYPE: RNA
<213> ORGANISM: Homo sapiens
<220> FEATURE:
<223> OTHER INFORMATION: Part of exon 17 of the human APP gene

<400> SEQUENCE: 35
guguucuuug cagaagau                                                   18

<210> SEQ ID NO 36
<211> LENGTH: 36
<212> TYPE: RNA
<213> ORGANISM: Homo sapiens
<220> FEATURE:
<223> OTHER INFORMATION: Part of intron16/exon17 of the human APP gene

<400> SEQUENCE: 36
ucuuaauuug uuuucaaggu guucuuugca gaagau                               36

<210> SEQ ID NO 37
<211> LENGTH: 39
<212> TYPE: RNA
<213> ORGANISM: Artificial Sequence
<220> FEATURE:
<223> OTHER INFORMATION: Description of Artificial Sequence: Synthetic
      QRX-203h (39) sequence

<400> SEQUENCE: 37
accuuuguuu gaacccacau cuucugcaaa gaacaccuu                            39

<210> SEQ ID NO 38
<211> LENGTH: 36
<212> TYPE: RNA
<213> ORGANISM: Artificial Sequence
<220> FEATURE:
<223> OTHER INFORMATION: Description of Artificial Sequence: Synthetic
      QRX-203h (36) sequence

<400> SEQUENCE: 38
uuuguuugaa cccacaucuu cugcaaagaa caccuu                               36

<210> SEQ ID NO 39
<211> LENGTH: 33
<212> TYPE: RNA
<213> ORGANISM: Artificial Sequence
<220> FEATURE:
<223> OTHER INFORMATION: Description of Artificial Sequence: Synthetic
      QRX-203h (33) sequence

<400> SEQUENCE: 39
```

```
guuugaaccc acaucuucug caaagaacac cuu                          33
```

<210> SEQ ID NO 40
<211> LENGTH: 30
<212> TYPE: RNA
<213> ORGANISM: Artificial Sequence
<220> FEATURE:
<223> OTHER INFORMATION: Description of Artificial Sequence: Synthetic
      QRX-203h (30) sequence

<400> SEQUENCE: 40

```
ugaacccaca ucuucugcaa agaacaccuu                              30
```

<210> SEQ ID NO 41
<211> LENGTH: 27
<212> TYPE: RNA
<213> ORGANISM: Artificial Sequence
<220> FEATURE:
<223> OTHER INFORMATION: Description of Artificial Sequence: Synthetic
      QRX-203h (27) sequence

<400> SEQUENCE: 41

```
acccacaucu ucugcaaaga acaccuu                                 27
```

<210> SEQ ID NO 42
<211> LENGTH: 39
<212> TYPE: RNA
<213> ORGANISM: Artificial Sequence
<220> FEATURE:
<223> OTHER INFORMATION: Description of Artificial Sequence: Synthetic
      QRX-203m (39) sequence

<400> SEQUENCE: 42

```
gccuuuguuc gaacccacau cuucagcaaa gaacaccuu                    39
```

<210> SEQ ID NO 43
<211> LENGTH: 36
<212> TYPE: RNA
<213> ORGANISM: Artificial Sequence
<220> FEATURE:
<223> OTHER INFORMATION: Description of Artificial Sequence: Synthetic
      QRX-203m (36) sequence

<400> SEQUENCE: 43

```
uuuguucgaa cccacaucuu cagcaaagaa caccuu                       36
```

<210> SEQ ID NO 44
<211> LENGTH: 33
<212> TYPE: RNA
<213> ORGANISM: Artificial Sequence
<220> FEATURE:
<223> OTHER INFORMATION: Description of Artificial Sequence: Synthetic
      QRX-203m (33) sequence

<400> SEQUENCE: 44

```
guucgaaccc acaucuucag caaagaacac cuu                          33
```

<210> SEQ ID NO 45
<211> LENGTH: 30
<212> TYPE: RNA
<213> ORGANISM: Artificial Sequence
<220> FEATURE:
<223> OTHER INFORMATION: Description of Artificial Sequence: Synthetic
      QRX-203m (30) sequence

<400> SEQUENCE: 45

```
cgaacccaca ucuucagcaa agaacaccuu                              30
```

<210> SEQ ID NO 46
<211> LENGTH: 27
<212> TYPE: RNA
<213> ORGANISM: Artificial Sequence
<220> FEATURE:
<223> OTHER INFORMATION: Description of Artificial Sequence: Synthetic
    QRX-203m (27) sequence

<400> SEQUENCE: 46
acccacaucu ucagcaaaga acaccuu                                              27

<210> SEQ ID NO 47
<211> LENGTH: 26
<212> TYPE: RNA
<213> ORGANISM: Artificial Sequence
<220> FEATURE:
<223> OTHER INFORMATION: Description of Artificial Sequence: Synthetic
    AON1-2-1 sequence

<400> SEQUENCE: 47
ccacaucuuc ugcaaagaac accuug                                               26

<210> SEQ ID NO 48
<211> LENGTH: 30
<212> TYPE: RNA
<213> ORGANISM: Artificial Sequence
<220> FEATURE:
<223> OTHER INFORMATION: Description of Artificial Sequence: Synthetic
    AON1-4-1 sequence

<400> SEQUENCE: 48
aucuucugca aagaacaccu ugaaaacaaa                                           30

<210> SEQ ID NO 49
<211> LENGTH: 34
<212> TYPE: RNA
<213> ORGANISM: Artificial Sequence
<220> FEATURE:
<223> OTHER INFORMATION: Description of Artificial Sequence: Synthetic
    AON1-4-2 sequence

<400> SEQUENCE: 49
ccacaucuuc ugcaaagaac accuugaaaa caaa                                      34

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
    Forward primer

<400> SEQUENCE: 50
tctgggctga caaacatcaa                                                      20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
    Reverse primer

<400> SEQUENCE: 51
ttctgctgca tcttggagag                                                      20

<210> SEQ ID NO 52
<211> LENGTH: 75
<212> TYPE: PRT
<213> ORGANISM: Homo sapiens
<220> FEATURE:
<223> OTHER INFORMATION: Exon 16 - Exon 17 - Exon 18 of APP

<400> SEQUENCE: 52

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu
65                  70                  75

<210> SEQ ID NO 53
<211> LENGTH: 26
<212> TYPE: PRT
<213> ORGANISM: Artificial Sequence
<220> FEATURE:
<223> OTHER INFORMATION: Description of Artificial Sequence: Synthetic
      Exon 16 - Exon 18 of APP sequence

<400> SEQUENCE: 53

Asp Ala Glu Phe Arg His Asp Ser Gly Tyr Glu Val His His Gln Lys
1               5                   10                  15

Leu Val Asp Ala Ala Val Thr Pro Glu Glu
            20                  25

<210> SEQ ID NO 54
<211> LENGTH: 14
<212> TYPE: PRT
<213> ORGANISM: Homo sapiens
<220> FEATURE:
<223> OTHER INFORMATION: APP

<400> SEQUENCE: 54

Thr Glu Glu Ile Ser Glu Val Lys Met Asp Ala Glu Phe Arg
1               5                   10

<210> SEQ ID NO 55
<211> LENGTH: 5
<212> TYPE: PRT
<213> ORGANISM: Homo sapiens
<220> FEATURE:
<223> OTHER INFORMATION: APP

<400> SEQUENCE: 55

His Gln Lys Leu Val
1               5

<210> SEQ ID NO 56
<211> LENGTH: 5
<212> TYPE: PRT
<213> ORGANISM: Homo sapiens
<220> FEATURE:
<223> OTHER INFORMATION: APP

<400> SEQUENCE: 56

Val Gly Ser Asn Lys

-continued

```
<210> SEQ ID NO 57
<211> LENGTH: 15
<212> TYPE: PRT
<213> ORGANISM: Homo sapiens
<220> FEATURE:
<223> OTHER INFORMATION: APP

<400> SEQUENCE: 57

Thr Val Ile Val Ile Thr Leu Val Met Leu Lys Lys Lys Gln Tyr
1               5                   10                  15

<210> SEQ ID NO 58
<211> LENGTH: 5
<212> TYPE: PRT
<213> ORGANISM: Homo sapiens
<220> FEATURE:
<223> OTHER INFORMATION: APP

<400> SEQUENCE: 58

Glu Gln Met Gln Asn
1               5

<210> SEQ ID NO 59
<211> LENGTH: 34
<212> TYPE: PRT
<213> ORGANISM: Homo sapiens
<220> FEATURE:
<223> OTHER INFORMATION: APP

<400> SEQUENCE: 59

Val Gly Ser Asn Lys Gly Ala Ile Ile Gly Leu Met Val Gly Gly Val
1               5                   10                  15

Val Ile Ala Thr Val Ile Val Ile Thr Leu Val Met Leu Lys Lys Lys
            20                  25                  30

Gln Tyr

<210> SEQ ID NO 60
<211> LENGTH: 199
<212> TYPE: RNA
<213> ORGANISM: Homo sapiens
<220> FEATURE:
<223> OTHER INFORMATION: exon 17 of human APP and flanking regions

<400> SEQUENCE: 60 cuuuucuua auuguuuuc aaggguucu uugcagaaga ugugguuca aacaaaggug      60 caaucauugg acucauggug ggcguguug ucauagcgac agugaucguc aucaccuugg  120
ugaugcugaa gaagaaacag uacacaucca uucaucaugg ugugguggag guagguaaac 180
uugacugcau guuccaag                                               199

<210> SEQ ID NO 61
<211> LENGTH: 4
<212> TYPE: PRT
<213> ORGANISM: Homo sapiens

<400> SEQUENCE: 61

Arg His Asp Ser
1

<210> SEQ ID NO 62
<211> LENGTH: 22
<212> TYPE: RNA
```

<213> ORGANISM: Homo sapiens

<400> SEQUENCE: 62
uuucaaggug uucuuugcag aa                                    22

<210> SEQ ID NO 63
<211> LENGTH: 22
<212> TYPE: RNA
<213> ORGANISM: Homo sapiens

<400> SEQUENCE: 63
agaugugggu ucaaacaaag gu                                    22

<210> SEQ ID NO 64
<211> LENGTH: 24
<212> TYPE: RNA
<213> ORGANISM: Homo sapiens

<400> SEQUENCE: 64
gguucaaaca aaggugcaau cauu                                  24

<210> SEQ ID NO 65
<211> LENGTH: 21
<212> TYPE: RNA
<213> ORGANISM: Homo sapiens

<400> SEQUENCE: 65
ucauuggacu caugguggggc g                                    21

<210> SEQ ID NO 66
<211> LENGTH: 20
<212> TYPE: RNA
<213> ORGANISM: Homo sapiens

<400> SEQUENCE: 66
gguguuguca uagcgacagu                                       20

<210> SEQ ID NO 67
<211> LENGTH: 20
<212> TYPE: RNA
<213> ORGANISM: Homo sapiens

<400> SEQUENCE: 67
gcugaagaag aaacaguaca                                       20

<210> SEQ ID NO 68
<211> LENGTH: 20
<212> TYPE: RNA
<213> ORGANISM: Homo sapiens

<400> SEQUENCE: 68
acaguacaca uccauucauc                                       20

<210> SEQ ID NO 69
<211> LENGTH: 22
<212> TYPE: RNA
<213> ORGANISM: Homo sapiens

<400> SEQUENCE: 69
ugguggaggu agguaaacuu ga                                    22

<210> SEQ ID NO 70
<211> LENGTH: 24

```
<212> TYPE: RNA
<213> ORGANISM: Homo sapiens

<400> SEQUENCE: 70
ucuuaauuug uuuucaaggu guuc                                          24

<210> SEQ ID NO 71
<211> LENGTH: 25
<212> TYPE: RNA
<213> ORGANISM: Homo sapiens

<400> SEQUENCE: 71
ucaagguguu cuuugcagaa gaugu                                         25

<210> SEQ ID NO 72
<211> LENGTH: 25
<212> TYPE: RNA
<213> ORGANISM: Homo sapiens

<400> SEQUENCE: 72
uguuuucaag guguucuuug cagaa                                         25

<210> SEQ ID NO 73
<211> LENGTH: 30
<212> TYPE: RNA
<213> ORGANISM: Homo sapiens

<400> SEQUENCE: 73
uuuguuuuca agguguucuu ugcagaagau                                    30
```